US010532298B2

(12) United States Patent
Sinha et al.

(10) Patent No.: US 10,532,298 B2
(45) Date of Patent: Jan. 14, 2020

(54) METHOD FOR SEPARATING SOLID PARTICLES FROM A WATERBODY

(71) Applicant: RELIANCE INDUSTRIES LIMITED, Mumbai (IN)

(72) Inventors: Avinash Sinha, Greater Noida (IN); Sairam Malladi, Hyderabad (IN); Ninad Pramod Gujarathi, Pune (IN); Ashwin Govindaji Gajra, Mumbai (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/532,251

(22) PCT Filed: Dec. 2, 2015

(86) PCT No.: PCT/IB2015/059289
§ 371 (c)(1),
(2) Date: Jun. 1, 2017

(87) PCT Pub. No.: WO2016/088057
PCT Pub. Date: Jun. 9, 2016

(65) Prior Publication Data
US 2017/0266587 A1    Sep. 21, 2017

(30) Foreign Application Priority Data

Dec. 2, 2014   (IN) .......................... 1824/MUM/2014

(51) Int. Cl.
*B01D 21/01*   (2006.01)
*C02F 1/463*   (2006.01)
(Continued)

(52) U.S. Cl.
CPC ............. *B01D 21/01* (2013.01); *B01D 29/05* (2013.01); *B01D 29/52* (2013.01); *B01D 29/908* (2013.01);
(Continued)

(58) Field of Classification Search
None
See application file for complete search history.

(56) References Cited

U.S. PATENT DOCUMENTS 4,800,039 A * 1/1989 Hassick ................ C02F 1/5236
                                                    210/723
6,110,374 A * 8/2000 Hughes .................. B01D 39/16
                                                    210/638
(Continued)

FOREIGN PATENT DOCUMENTS

EP        2 397 541        12/2011
WO    WO-2012042524 A1 *   4/2012    ................ C02F 9/00

OTHER PUBLICATIONS

Tramfloc 552 MSDS—Tramfloc, Inc, May 30, 2015 (Year: 2015).*
International Search Report and Written Opinion issued for PCT/182015/059289, dated Apr. 25, 2016, 17 pages.

*Primary Examiner* — Bradley R Spies
(74) *Attorney, Agent, or Firm* — Foley & Lardner LLP

(57) ABSTRACT

The present disclosure relates to a method for separation of solid particles from a waterbody. Preferably, the present disclosure relates to a method, wherein a combination of chemicals including coagulant(s) and flocculant(s) are employed for said separation of solid particles, wherein suitable examples of solid particles are living organisms and non-living matter, wherein living organisms include autotrophs such as phototrophs, which are either microscopic or macroscopic in nature (algae). The disclosure thus particularly relates to method of chemical coagulation and flocculation for separating solid particles, preferably either algae (Continued)

US 10,532,298 B2
Page 2 or bacteria or both from a waterbody. The present disclosure also provides for an alternate method, wherein the aforesaid method of coagulation and flocculation is combined with electro-coagulation and/or pH modulation strategies for separation of said solid particles in any sequence.

12 Claims, 14 Drawing Sheets

(51) Int. Cl.

| | |
|---|---|
| *C02F 1/54* | (2006.01) |
| *C02F 1/66* | (2006.01) |
| *C02F 1/00* | (2006.01) |
| *C02F 1/24* | (2006.01) |
| *C02F 1/56* | (2006.01) |
| *C12M 1/00* | (2006.01) |
| *C12M 1/26* | (2006.01) |
| *B01D 29/05* | (2006.01) |
| *B01D 29/52* | (2006.01) |
| *B01D 29/90* | (2006.01) |
| *B01D 35/28* | (2006.01) |
| *B01D 39/10* | (2006.01) |
| *E02B 3/02* | (2006.01) |
| *E02F 7/06* | (2006.01) |
| *C02F 103/00* | (2006.01) |
| *B01D 37/00* | (2006.01) |

(52) U.S. Cl.
CPC ............. *B01D 35/28* (2013.01); *B01D 39/10* (2013.01); *C02F 1/463* (2013.01); *C02F 1/54* (2013.01); *C02F 1/66* (2013.01); *C12M 21/02* (2013.01); *C12M 33/22* (2013.01); *C12M 47/02* (2013.01); *E02B 3/023* (2013.01); *E02F 7/065* (2013.01); *B01D 37/00* (2013.01); *C02F 1/004* (2013.01); *C02F 1/24* (2013.01); *C02F 1/56* (2013.01); *C02F 2001/007* (2013.01); *C02F 2103/007* (2013.01); *C02F 2301/08* (2013.01)

(56) References Cited

U.S. PATENT DOCUMENTS

| | | | |
|---|---|---|---|
| 2009/0162919 A1 | 6/2009 | Radaelli et al. | |
| 2013/0341267 A1* | 12/2013 | Prasad | C02F 9/00 210/605 |
| 2015/0251932 A1* | 9/2015 | Laaroussi | C02F 1/463 205/701 |
| 2016/0176741 A1* | 6/2016 | Gao | C02F 1/40 210/712 |

* cited by examiner

METHOD FOR SEPARATING SOLID PARTICLES FROM A WATERBODY

CROSS-REFERENCE TO RELATED APPLICATIONS

The present application is a National Stage of PCT Application No. PCT/IB2015/059289, filed Dec. 2, 2015, which claims priority to Indian Patent Application No. 1824/MUM/2014, filed Dec. 2, 2014. The contents of both applications are hereby incorporated by reference in their entirety.

TECHNICAL FIELD

The present disclosure relates to a method for separation of solid particles from a waterbody. Particularly, the disclosure relates to method chemical coagulation and flocculation for separating solid particles from a waterbody. The present disclosure relates to employing a combination of chemicals in the form of coagulant(s) and flocculant(s) for said separation of solid particles, including but not limiting to living organisms and non-living matter. In an alternative embodiment, the present disclosure describes the separation of solid particles by combining the said method of chemical coagulation and flocculation with electro-coagulation and/or pH modulation.

BACKGROUND OF THE DISCLOSURE

Conventionally, various methods have been employed to separate solid particles from a waterbody, which included sedimentation, filtration, centrifugation etc. However, said methods have their own limitations when it comes to handling large volumes while separating the solid particles from a waterbody. Further, coagulants and flocculants have been traditionally used in sedimentation, filtration through granular and fluidized (blanket) media, centrifugation, vacuum and pressure filtration, dissolved air flotation and other phase separation processes to enhance the separation. However, there have been common disadvantages of these coagulants while it is being employed with conventional methods such as sedimentation, filtration, centrifugation etc. The conventional coagulants are characterized by high level of swelling and retention of large volume of fluid and they are not entirely stable and tend to produce hydroxide precipitate which considerably reduces the coagulating properties.

Furthermore, to increase phase separation process efficiency during the process of separation, some flocculants such as activated silicic acid have been added to the coagulants. However, addition of such flocculants to the waterbody comprising solid particles requires slow agitation because the formed large flocks often break into smaller flocks by strong agitation. Further, it has been observed that large amount of flocculants and coagulants are required for effective floc-formation. However, since liquid solution of the polymer flocculant has high viscosity, it is difficult to uniformly diffuse the flocculant into the waterbody by slow agitation. In case of employing slow agitation for the purpose of preventing the flocks from being broken into small flocks, it takes a long time to diffuse the polymer flocculant and it causes irregularity in adhesion of the polymer flocculant on the surface of the solid particles and thus sufficient flocculation function cannot be obtained. As a result, an increase in the amount of the polymer flocculant or coagulant added is required.

However, such high dosages of coagulant and flocculant present two fold problems: i) rise in the cost of chemicals, and ii) high chemical content in downstream processing, which would in turn increase the cost of further separation. Nonetheless, the use of waterbody is unavoidable for certain applications such as commercial cultivation of solid particles including but not limiting to living organisms and non-living matter. Hence, there has been a long felt need to overcome the limitation observed in the separation of solid particles from a waterbody.

Separation of solid particles including but not limiting to living organisms and non-living matter from their environments such as waterbody has been a challenge for a long time. Living organisms that are usually found in waterbody include Phototrophs or Photoautotrophs, which are autotrophic organisms that carry out photon capture to acquire energy. A non-limiting example of such organism is algae, a very large and diverse group of simple organisms, ranging from unicellular to multicellular forms.

Currently, the most economically viable method of cultivating such organisms employs the use of open raceways. However, the areal productivity as well as the concentration of such microorganisms in such raceways is extremely low. Harvesting or separation of such organisms from their growth medium per se is technically possible using physical separation methods such as centrifugation and filtration in a single step. However, a very large volume of dilute micro suspension will have to be handled to separate very small amounts of solid organisms. This makes application of physical separation technologies for harvesting of organisms such as algae economically non-viable and extremely challenging. As a result, presently about 30% of the total production cost is attributed to separation or harvesting. The challenge in such separation/harvesting is thus to develop a method that can significantly reduce the fluid volume to be handled or increase the solid concentration resulting in a slurry that can then be handled viably at the secondary harvesting step. As an answer to the above said limitations in the separation of solid particles including but not limiting to living organisms and non-living matter, the Applicants of the instant invention intend to arrive at a distinct method for separation of solid particles from a waterbody.

STATEMENT OF THE DISCLOSURE

The present disclosure relates to a method for separation of solid particles from waterbody, said method comprising step of contacting or subjecting the waterbody to a combination of chemicals or techniques or both, selected from a group comprising coagulant, flocculant, electro-coagulation and pH modulation or any combination thereof.

The present disclosure relates to a method for separation of solid particles from a waterbody, wherein the said method employs a unique combination of chemicals for said separation of solid particles.

The present disclosure further relates to a method for employing the combination of chemicals, including but not limiting to coagulant(s) and flocculant(s) for separation of solid particles.

In an exemplary embodiment, the disclosure relates to a method for separating solid particles from a waterbody, wherein the solid particles are living organisms and non-living matter, wherein the living organisms includes but not limiting to autotrophs such as phototrophs. In another embodiment, said living organisms are either microorganisms or macroorganisms, and the waterbody consists of any one or more of any such organisms and/or non-living matter.

In an alternative embodiment of the present disclosure, the method of separating solid particles including but not limiting to living organisms and non-living matter, is performed by combining modulation of pH while employing the combination of chemicals such as coagulant(s) and flocculant(s).

In another alternative embodiment of the present disclosure, the method of separating solid particles including but not limiting to living organisms and non-living matter, is performed by combining providing electric impetus while employing the combination of chemicals such as coagulant(s) and flocculant(s).

In yet another alternative embodiment of the present disclosure, the method of separating solid particles including but not limiting to living organisms and non-living matter, performed by combining modulation of pH and providing electric impetus while employing the combination of chemicals such as coagulant(s) and flocculant(s), wherein in the method of separating solid particles steps of pH modulation, providing electric impetus and combination of said chemicals such as coagulant (s) and flocculant (s) is performed either in a predetermined sequence or in any order thereof which a skilled artisan is aware of for effective separation of solid particles and it is within the scope of this disclosure.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a description below are incorporated in and form part of the specification, and serve to further illustrate the embodiments and explain various principles and advantages, in accordance with the present disclosure where:

FIG. 1 illustrates the action of coagulant(s) and flocculant(s) combination on a waterbody comprising solid particles, wherein A) represents waterbody comprising said solid particles; B) represents pin flock formation after addition of coagulant(s); C) represents aggregation of pin flocks to form larger flocks after addition of flocculant(s); and D) represents settled flock of solid particles after stirring is stopped.

Figure 9:
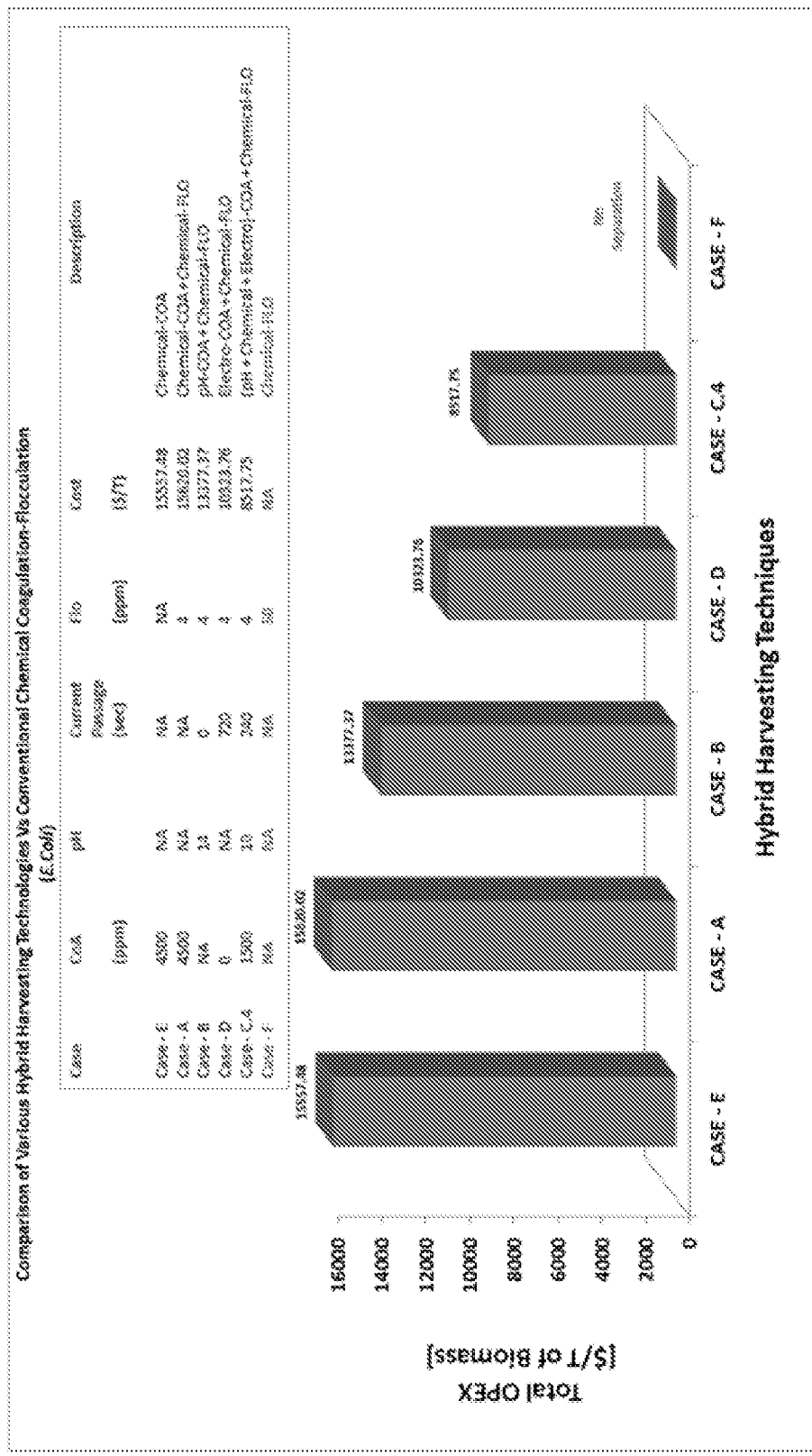

FIG. 9 illustrates the comparison of the operating cost (OPEX) of the methods such as chemical coagulation (Case-E), chemical coagulation and chemical flocculation (Case-A), pH modulated coagulation and flocculation (Case-B), electro-coagulation and chemical flocculation (Case-D), pH modulation, electro-coagulation and chemical coagulation and flocculation (Case-C4) and Chemical flocculation (Case-F), for separation of bacteria such as *E. coli* from a waterbody such as fresh water.

Figure 10:
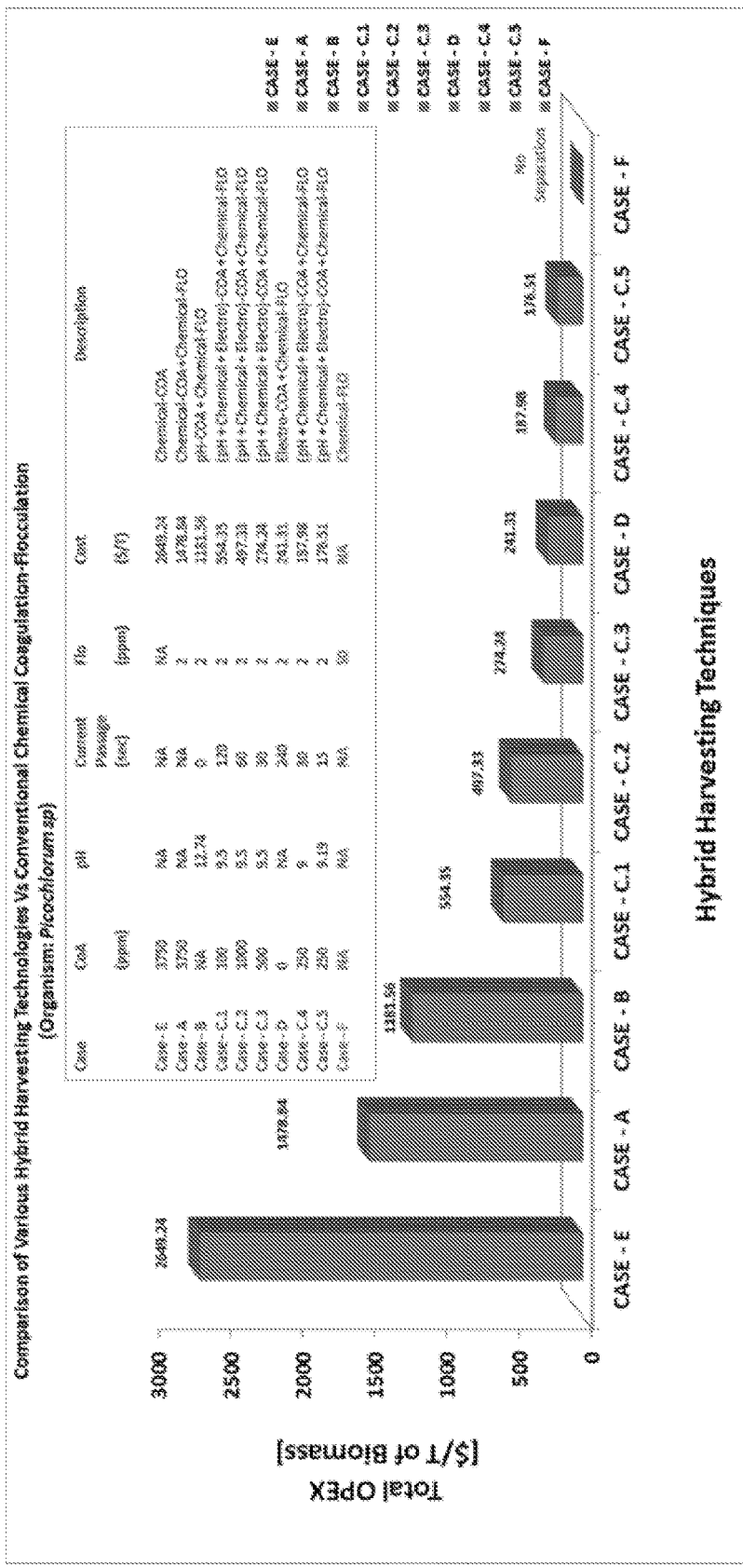

FIG. 10 illustrates comparison of the operating cost (OPEX) for separation of algal species such as *Picochlorum* sp by techniques such as chemical coagulation, chemical coagulation and chemical flocculation, pH modulated coagulation and flocculation, electro-coagulation and chemical flocculation, pH modulation, electro-coagulation and chemical coagulation and flocculation and Chemical flocculation.

Figure 11:
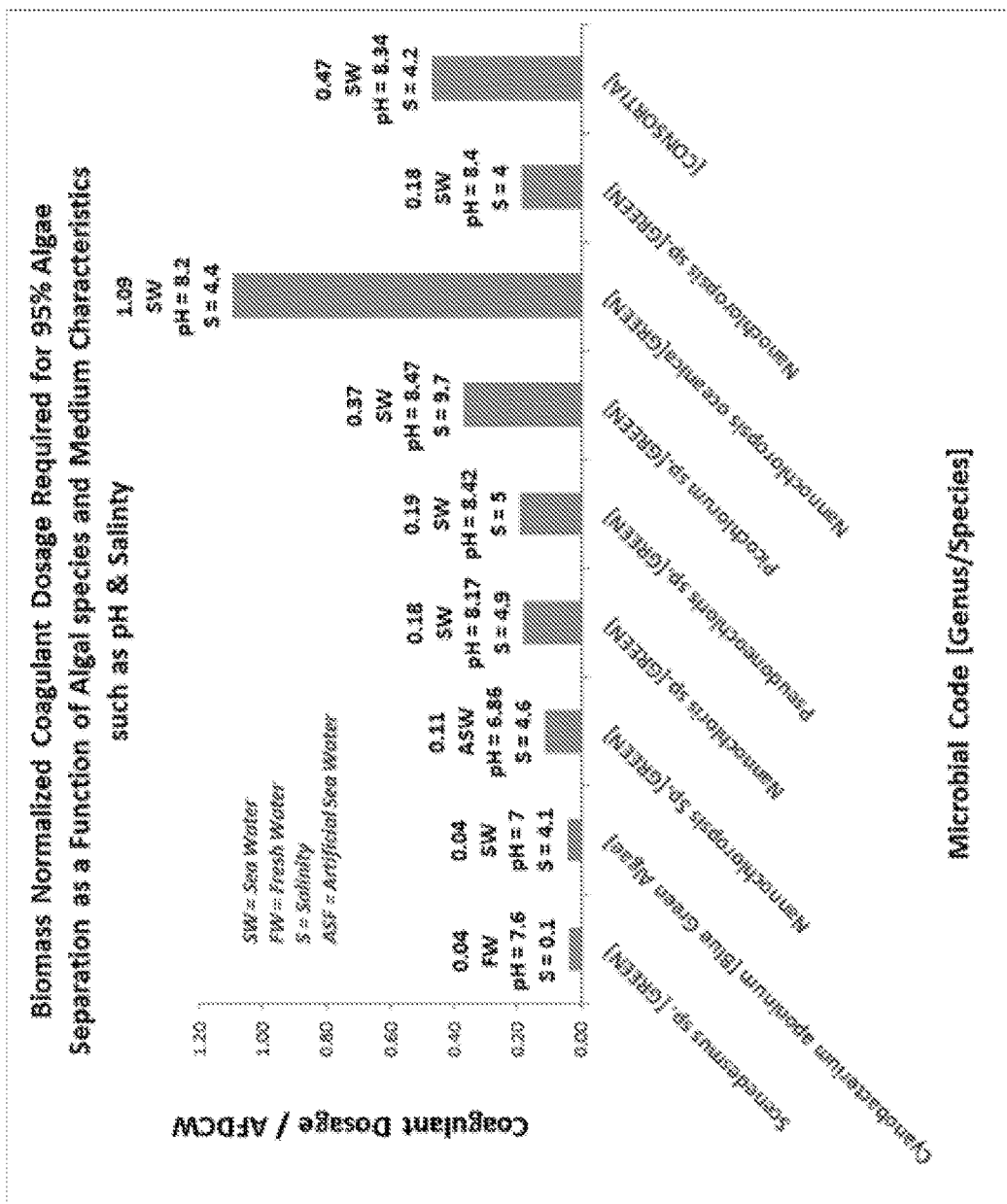

FIG. 11 illustrates biomass normalized coagulant dosage required for 95% algae separation as a function of algal species and parameters.

Figure 12:
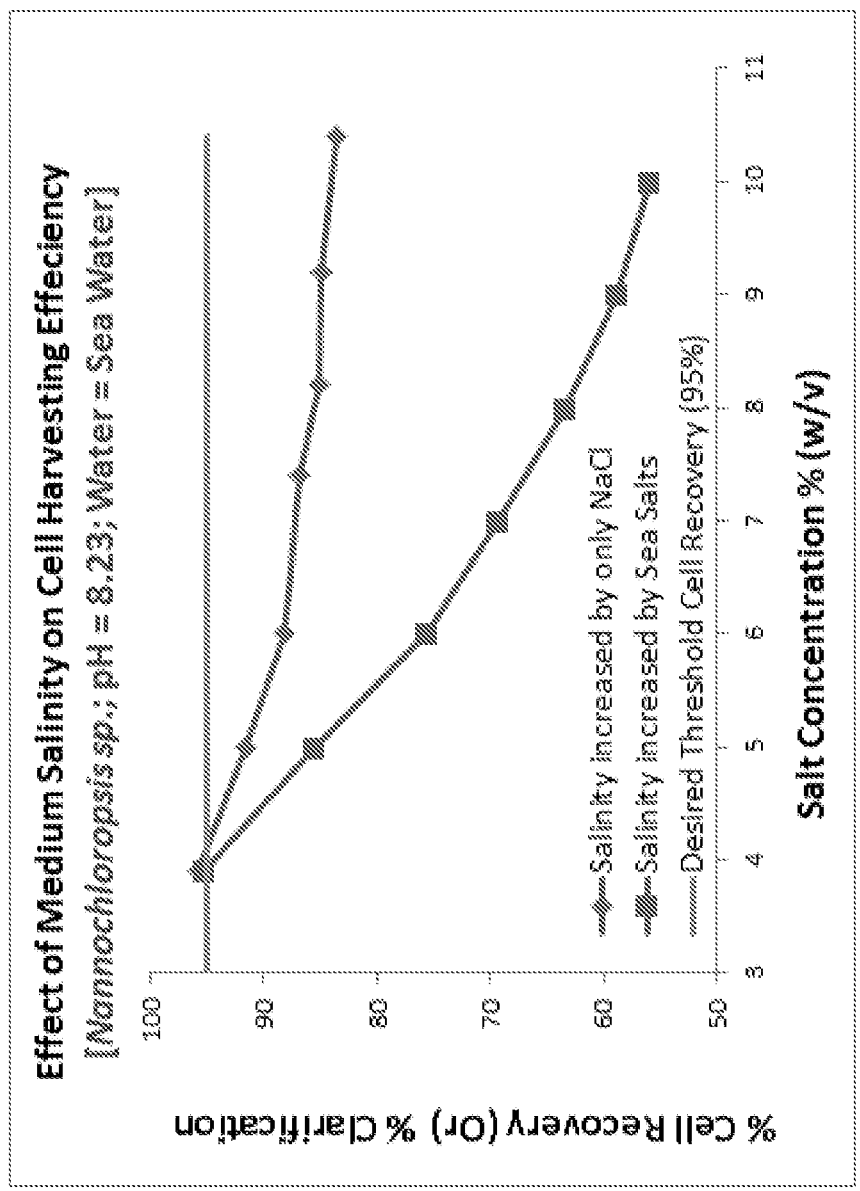

FIG. 12 illustrates the effect of medium salinity measured in terms of sodium chloride (NaCl) and sea salts on coagulant dosage required for achieving 95% cell recovery/harvesting for *Nannochloropsis* sp.

Figure 13:
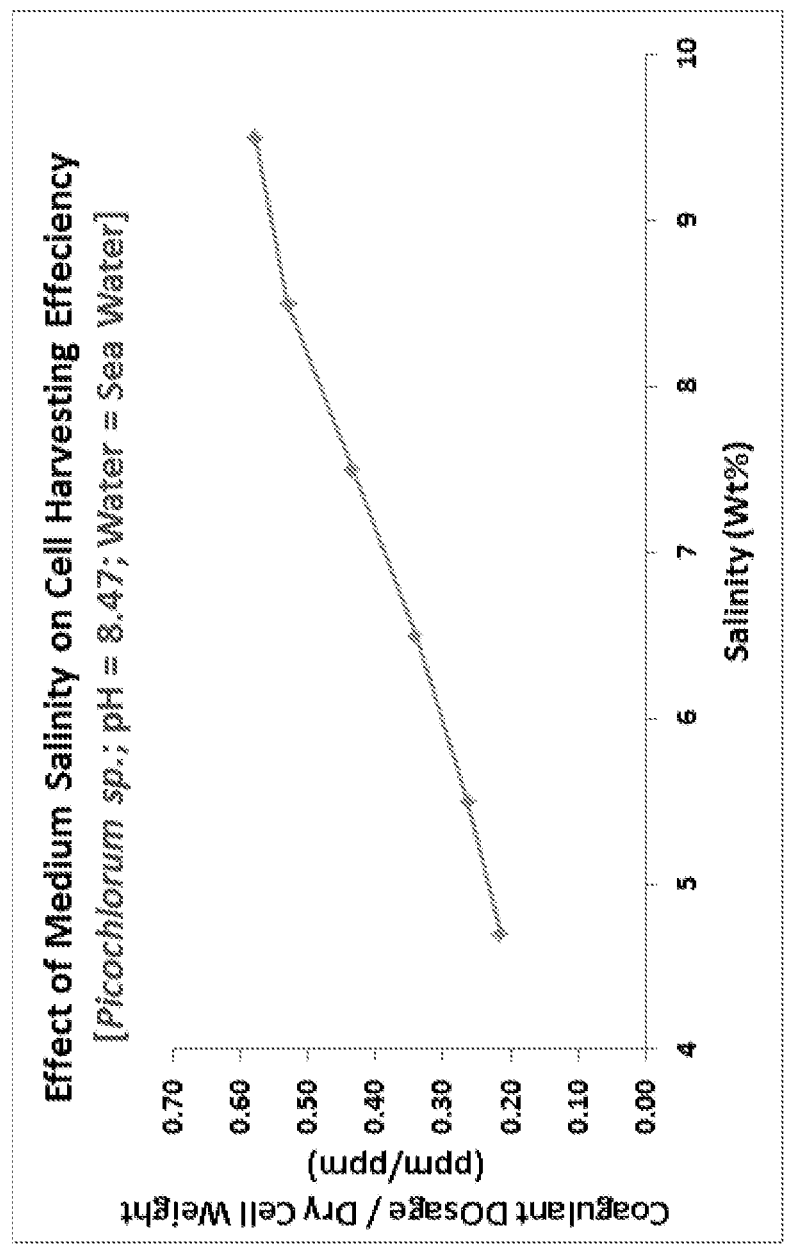

FIG. 13 illustrates the effect of medium salinity measured in terms of sodium chloride (NaCl) and sea salts on coagulant dosage required for achieving 95% cell recovery/harvesting for *Picochlorum* sp.

Figure 14:
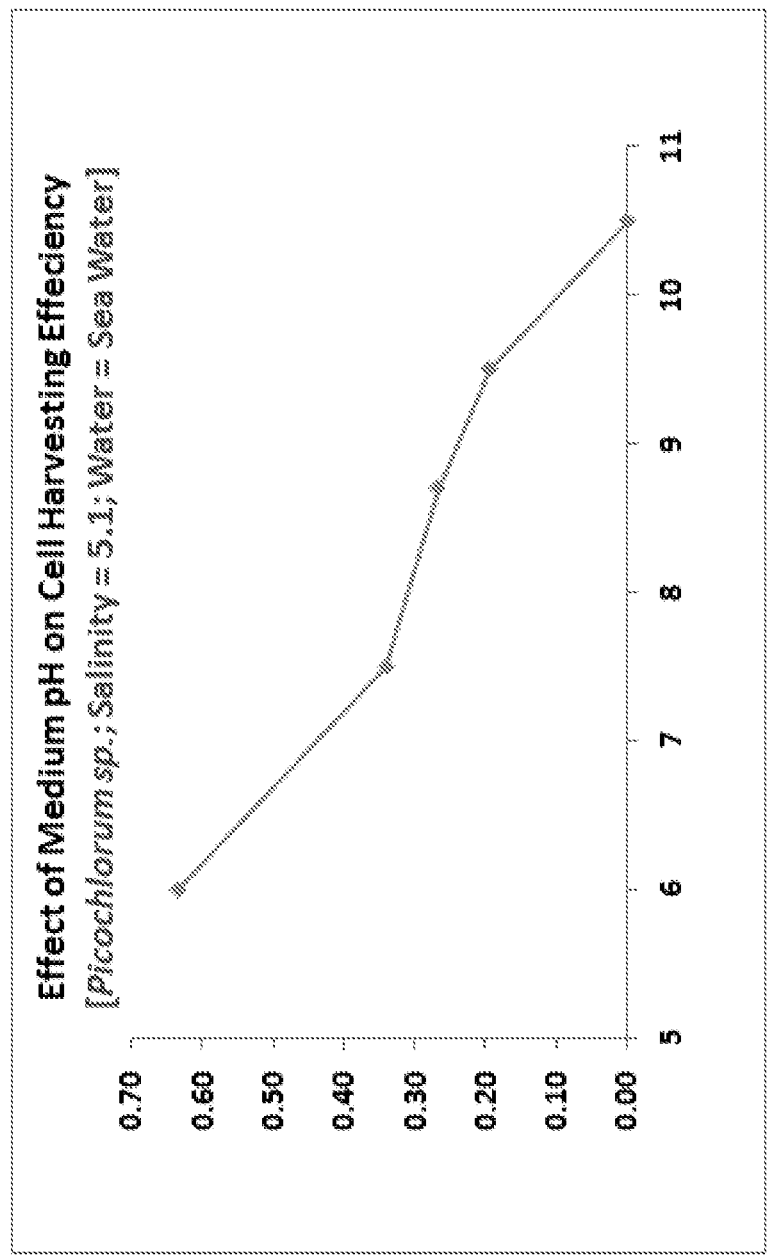

FIG. 14 illustrates medium pH on coagulant dosage required for achieving 95% cell recovery/harvesting for *Picochlorum* sp.

Figure 15:
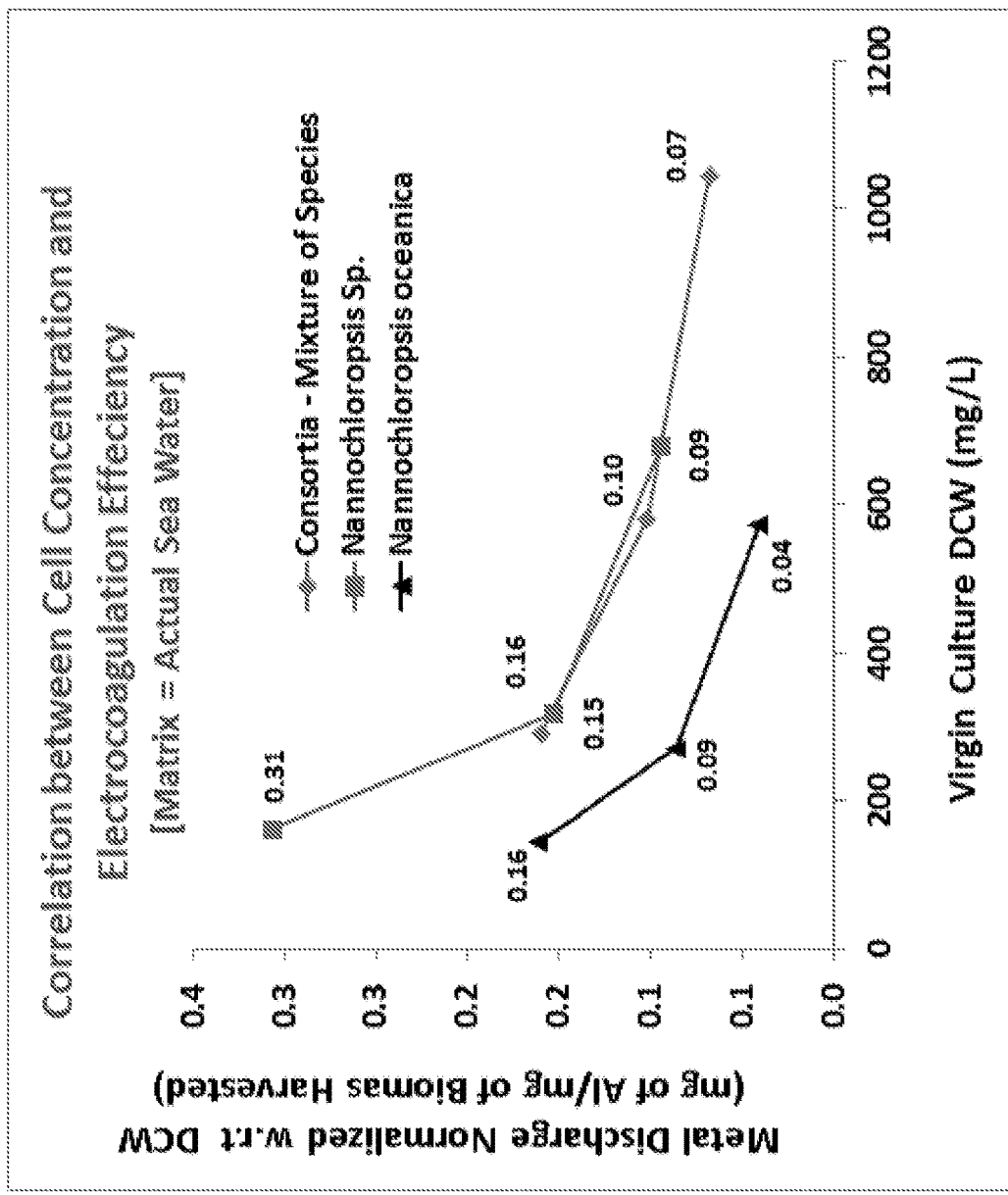

FIG. 15 illustrates the effect of cell concentration on coagulation efficiency in the electrocoagulation for achieving 95% cell recovery for *Nannochloropsis* sp, *Nannochloropsis oceanica* and consortia of algal species.

Figure 16:
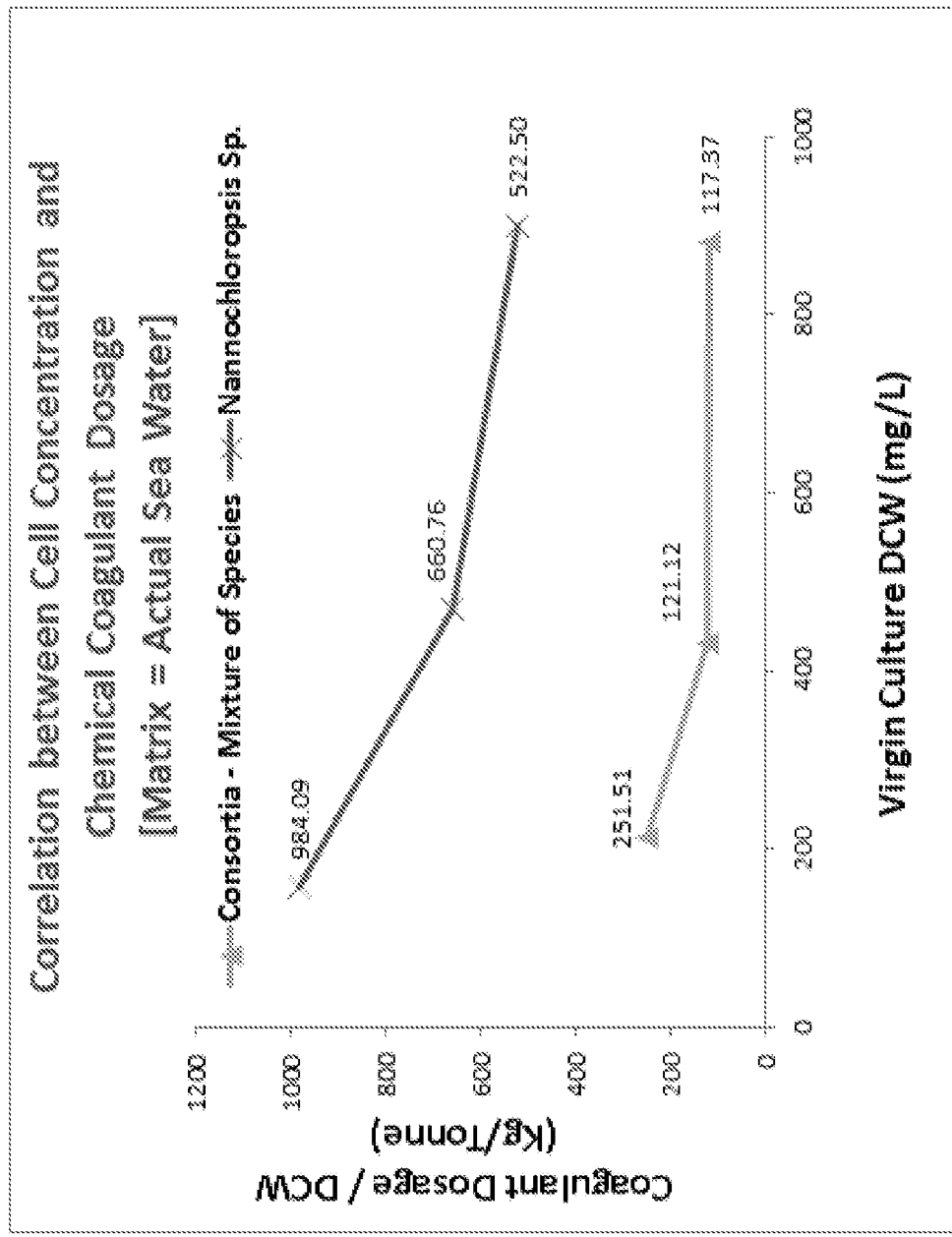

FIG. 16 illustrates the effect of cell concentration on coagulation in chemical coagulation and chemical flocculation for achieving 95% cell recovery for *Nannochloropsis* sp and consortia of algal species.

Figure 17:
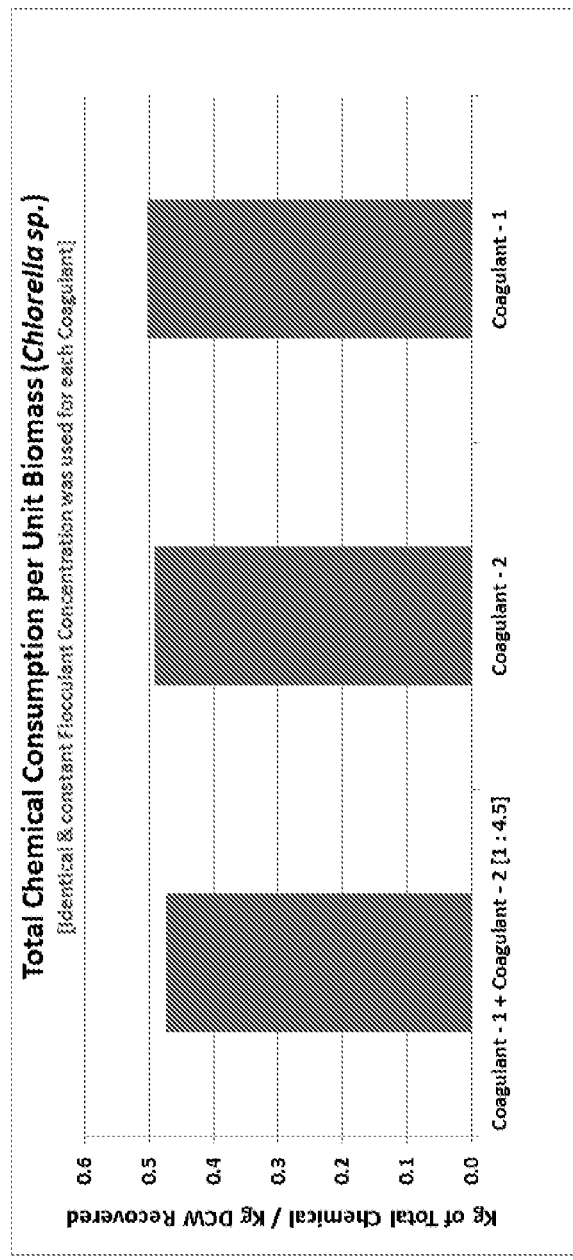

FIG. 17 illustrates the effect of usage of two coagulants vis-à-vis one coagulant in the methods of the instant disclosure.

DETAILED DESCRIPTION OF THE DISCLOSURE

To overcome the non-limited drawbacks of the prior art and to provide for simple, cost-effective and efficient method for separation of solid particles including but not limiting to living organism and non-living matter from the environment, preferably waterbody, the present disclosure provides a method of separating solid particles by a unique combination of chemicals including but not limiting to coagulant(s) and flocculant(s).

In an embodiment, the present disclosure relates to a method for separation of solid particles from waterbody, said method comprising step of contacting or subjecting the waterbody to a combination of chemicals or techniques or both, selected from a group comprising coagulant, flocculant, electro-coagulation and pH modulation or any combination thereof.

In another embodiment, the solid particles is a living solid particles selected from a group comprising algae and bacteria or a combination thereof, wherein the algae is selected from a group comprising *Scenedesmus* sp, *Cyanobacterium aponium, Nannochloropsis* sp, *Pseudooneochloris* sp, *Picochlorum* sp and *Nanochloropsis oceanica*, or any combination thereof, and wherein the bacteria is selected from a group comprising *E. coli*, Lacto bacilli, *Streptomyces, Bacillus*, actinomycetous bacteri, *Lactococcus Lacti, Spirochaet* and *Aquaspirillum*

In another embodiment, the waterbody is selected from a group comprising ocean water, sea water, lake water, pond water, wetland water and puddle water, or any combination thereof and wherein the salinity of the waterbody is ranging from about 0.1% to 14%.

In another embodiment, the coagulant is selected from a group comprising polyamines, aluminum chlorohydrate polyamines, aluminum chlorohydrate-polyaluminum chloride-polyacrylamide-polyamines, aluminum hydroxide chloride and blend of cationic polymer with poly aluminum hydroxide or any combination thereof; and the flocculant is selected from a group comprising polyacrylamide, copolymer of polyacrylamide, copolymer of acrylamide and sodium acrylate, acrylamide with cationic acrylic acid derivative, polyaluminum chloride and poly diallyl-dimethylammonium chloride, or any combination thereof.

In another embodiment, the coagulant is at a concentration ranging from about 5 ppm to 500 ppm with respect to concentration of the solid particles in the waterbody; and the flocculant is at a concentration ranging from about 0.5 ppm to 4 ppm with respect to concentration of the solid particles in the waterbody.

In another embodiment, percentage separation or recovery of the solid particles from the waterbody is at least 95%.

In another embodiment, the combination of at least one coagulant and at least one flocculant causes coagulation and flocculation, respectively of the solid particles in the waterbody.

In another embodiment, the method of separation of solid particles from the waterbody comprises step of contacting the waterbody having the solid particles with electric current, followed by contacting the waterbody with combination of at least one coagulant and at least one flocculant, wherein the electric current causes electro-coagulation of the solid particles and the at least one coagulant and the at least one flocculant causes coagulation and flocculation, respectively.

In another embodiment, the method of separation of solid particles from the waterbody comprises step of contacting the waterbody having the solid particles with at least one coagulant followed by contacting the waterbody with electric current, and at least one flocculant, wherein the electric current causes electro-coagulation of the solid particles and the at least one coagulant and the at least one flocculant causes coagulation and flocculation, respectively.

In another embodiment, the method of separation of solid particles from the waterbody comprises step of contacting the waterbody having the solid particles with electric current, followed by contacting the waterbody with at least one flocculant, wherein the electric current causes electro-coagulation of the solid particles and the at least one flocculant causes flocculation.

In another embodiment, the electric current is contacted with the waterbody having the solid particles for a time duration ranging from about 15 seconds to 720 seconds with respect to concentration of the solid particles in the waterbody.

In another embodiment, the method of separation of solid particles from the waterbody comprises step of modulating pH of the waterbody having the solid particles by addition of a base selected from a group comprising sodium hydroxide and potassium hydroxide or a combination thereof followed by contacting said waterbody with at least one coagulant and at least one flocculant, wherein the at least one coagulant and the at least one flocculant causes coagulation and flocculation, respectively.

In another embodiment, the modulated pH of the waterbody upon addition of the base is ranging from about 9.7 to 10.0 with respect to concentration of solid particles in the waterbody.

In another embodiment, the method of separation of solid particles from the waterbody comprises step of modulating pH of the waterbody having the solid particles by addition of a base selected from a group comprising sodium hydroxide, followed by contacting the waterbody with electric current, thereafter contacting the waterbody with combination of at least one coagulant and at least one flocculant, wherein the electric current causes electro-coagulation of the solid particles and the at least one coagulant and the at least one flocculant causes coagulation and flocculation, respectively.

In another embodiment, the method of separation of solid particles from the waterbody comprises step of modulating pH of the waterbody having the solid particles by addition of a base selected from a group comprising sodium hydroxide, followed by contacting the waterbody with at least one coagulant, followed by contacting the waterbody with electric current, and at least one flocculant, wherein the electric current causes electro-coagulation of the solid particles and the at least one coagulant and the at least one flocculant causes coagulation and flocculation, respectively.

In another embodiment, the method of separation of solid particles from the waterbody comprises step of modulating pH of the waterbody having the solid particles by addition of a base selected from a group comprising sodium hydroxide, followed by contacting the waterbody with electric current, and at least one flocculant, wherein the electric current causes electro-coagulation of the solid particles and the at least one flocculant causes flocculation.

In another embodiment, the electric current is contacted with the waterbody having the solid particles for a time duration ranging from about 15 seconds to 720 seconds with respect to concentration of the solid particles in the waterbody and wherein the modulated pH of the waterbody upon addition of the base is ranging from about 9.7 to 10.0 with respect to concentration of solid particles in the waterbody.

In another embodiment, the method comprises process selected from a group comprising dissolved air flotation, froth flotation and filtration for separation of solid particles from a waterbody upon contacting the waterbody with combination of at least one coagulant and at least one flocculant, optionally along with electro-coagulation or pH modulation or a combination thereof.

In another embodiment, the method reduces the coagulant and the flocculant dosage within the combination of the at least one coagulant and the at least one flocculant during the separation of the solid particles from the waterbody when compared to a method employing coagulant and flocculant, independently for separation of the solid particles.

In a non-limiting embodiment, the unique combination of coagulant(s) and flocculant(s) of the present disclosure are employed in a method for separating solid particles from a waterbody including but not limiting to fresh water and marine water or a combination thereof.

In an exemplary embodiment, the unique combination of coagulant(s) and flocculant(s) of the instant method are employed in a method for separating solid particles from a waterbody, wherein the solid particles are living organisms and non-living matter, wherein the living organism includes but not limiting to autotrophs such as phototrophs.

In another embodiment, said living organisms are either microorganisms or macroorganisms, and the waterbody consists of any one or more of any such living organisms and/or non-living matter.

In a preferred embodiment, the unique combination of chemicals including but not limiting to coagulant(s) and flocculant(s) of the instant disclosure are employed in a method for separating microorganisms from a waterbody, wherein the waterbody is including but not limiting to fresh water and marine water.

In an exemplary embodiment, the unique combination of chemicals including but not limiting to coagulant(s) and flocculant(s) of the instant disclosure are employed in a method for separating microorganisms including but not limiting to algae, protists, phytoplankton and cyanobacteria from a waterbody, wherein the waterbody is including but not limiting to fresh water and marine water.

In yet another exemplary embodiment, the unique combination of chemicals including but not limiting to coagulant(s) and flocculant(s) of the instant disclosure are employed in a method for separating solid particles having negative charge on their surface, such as living organisms, including autotrophs such as phototrophs; and wherein such organisms are either microscopic or macroscopic in nature.

In an embodiment, the unique combination of coagulant(s) and flocculant(s) are employed in a method for separating solid particle from a waterbody having salinity ranging from about 0.1% to 14%. In an exemplary embodiment, the salinity of the waterbody from which solid particles are separated by the method of the instant disclosure is 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 10.2%, 10.4%, 10.6%, 10.8%, 11.0%, 11.2%, 11.4%, 11.6%, 11.8%, 12.0%, 12.2%, 12.4%, 12.6%, 12.8%, 13.0%, 13.2%, 13.4%, 13.6%, 13.8%, 14.0%.

In an embodiment, the present disclosure relates to a method of separating solid particles by coagulation and flocculation upon employing the unique combination of chemicals including but not limiting to coagulant(s) and flocculant(s).

In another embodiment, the chemical coagulation and flocculation of the instant disclosure is a cost effective and efficient method for separating solid particles from a waterbody, wherein the solid particles are living organisms and non-living matter and wherein living organism includes but not limiting to autotrophs such as phototrophs. In another embodiment, said living organisms are either microorganisms or macroorganisms, and the waterbody consists of any one or more of any such organisms and/or non-living matter.

In an embodiment, the natural environment including but not limiting to fresh water and marine water, from which said organisms are separated or harvested, comprise a high salinity in the range of about 0.1% to about 14%.

In a non-limiting embodiment of the present disclosure, the unique combination of chemicals including but not limiting to coagulant(s) and flocculant(s) employed in the method of the instant disclosure facilitates agglomeration of solid particles, wherein suitable examples of the solid particles are living organisms, including autotrophs such as phototrophs; and wherein such organisms are either microscopic or macroscopic in nature. In another embodiment, the terms coagulant(s) and flocculant(s) employed in the instant invention must be understood to mean a combination of singular coagulant or multiple coagulants and singular flocculant or multiple flocculants, unless otherwise explicitly recited.

In an exemplary embodiment, the unique combination of coagulant(s) and flocculant(s) employed in the instant disclosure comprises plurality of coagulant and flocculant in any amount or ratio or concentration within the scope of this disclosure.

In an exemplary embodiment of the present disclosure, the coagulant includes but is not limited to a cationic polymer, preferably strongly cationic medium molecular weight organic polymer, strongly cationic low molecular weight organic polymer, a polymer blend comprising inorganic metal salts and/or organic polymers or a combination thereof. In an embodiment, the strongly cationic coagulant within the present disclosure represents a coagulant having high charge density, and may have medium or low molecular weight.

In a preferred embodiment, the coagulant belongs to a general class of compounds including but not limiting to polyamines, derivatives of polyamines, aluminum chlorohydrate-polyamines, aluminum-chlorohydrate-polyaluminum, chloride-polyacrylamide-polyamines, blend of polyamines, poly aluminum chloride and blend of cationic polymers with poly aluminum hydroxide chloride, or any combination thereof.

In another preferred embodiment, the coagulants of the instant disclosure are high charge density cationic medium molecular weight organic polymers or polymer blends blended with aluminum hydroxide chloride. In a non-limiting embodiment the coagulants of the instant disclosure belongs general class of compounds selected from a group comprising aluminum chlorohydrate polyamines, polyamines, aluminum chlorohydrate-polyaluminum chloride-polyacrylamide-polyamines and aluminum hydroxide chloride.

In a most preferred embodiment, the coagulant employed in the methods of the instant disclosure is aluminum hydroxide chloride.

In an exemplary embodiment of the present disclosure, the flocculant includes but is not limited to an anionic polymer, preferably strongly anionic high molecular weight polymer. In an embodiment, the strongly anionic flocculant within the present disclosure represents a flocculant having high charge density, and having high molecular weight.

In a preferred embodiment, the flocculant belongs to a general class of compounds including but not limiting to polyacrylamide, copolymer of polyacrylamide, copolymer of acrylamide and sodium acrylate, acrylamide with cationic acrylic acid derivative, polyaluminum chloride and Poly Diallyl-dimethylammonium Chloride, or any combination thereof.

In a most preferred embodiment, flocculant employed in the methods of the instant disclosure is polyacrylamide.

In a non-limiting embodiment of the present disclosure, in the unique combination of coagulant(s) and flocculant(s) employed in the method of the instant disclosure for separating solid particles including but not limiting to living organism and non-living matter, the flocculant is at a concentration ranging from about 0.5 to 4 ppm for about 500 to 5000 ppm of solid particles in the waterbody and coagulant is at a concentration ranging from about 5 ppm to 500 ppm for about 500 ppm to 5000 ppm of solid particles in the waterbody.

In a non-limiting embodiment of the present disclosure, in the unique combination of coagulant and flocculant employed in the method of the instant disclosure for separating solid particles including microorganisms such as algae, the flocculant is at a concentration ranging from about 0.5 ppm to 4 ppm for about 500 to 5000 ppm of algae in the waterbody and coagulant is at a concentration ranging from about 5 ppm to 500 ppm for about 500 ppm to 5000 ppm of algae in the waterbody.

In an exemplary embodiment, the percentage recovery of solid particles, including but not limiting to living organisms and non-living matter from a waterbody upon employing the methods of the present disclosure is at least 95% with respect to the unique combination of coagulant and flocculant employed in the methods of the instant disclosure.

In an exemplary embodiment, the present disclosure relates to a method of separating solid particles, wherein suitable examples of solid particles are living organisms, including but not limiting to autotrophs such as phototrophs; and wherein such organisms are either microscopic or macroscopic in nature from a non-limiting fresh water or marine water by employing unique combination of chemicals including but not limiting to coagulant(s) and flocculant(s) of present disclosure through a process of coagulation and flocculation, wherein the said combination in the said method comprises a single dosage or multiple dosage of any one or both of coagulant(s) and flocculant(s).

In a non-limiting embodiment, the present disclosure provides for combining chemicals including but not limiting to coagulant(s) and flocculants(s) in any sequence and for any time period thereof within the scope of this disclosure. Said process of combining of chemicals including but not limiting to coagulant(s) and flocculants(s) provide separation of solid particles, wherein the solid particles are living organisms including but not limiting to autotrophs such as phototrophs; and wherein such organisms are either microorganisms or macroorganisms, from waterbody including but not limiting to fresh water and marine water, through process of coagulation and flocculation, also known as "chemical coagulation and chemical flocculation" or "chemical coagulation-flocculation" in the method of the present disclosure.

In a non-limiting embodiment, the present disclosure provides for a method of combining chemicals including but not limiting to coagulant(s) and flocculant(s) for separation of solid particles, including but not limiting to living organisms and non-living matter, from a waterbody including but not limiting to fresh water and marine water by coagulation and flocculation, wherein said method comprises non-limiting acts of—
  a. contacting at least one coagulant(s) with the water body in one or more dosages, and mixing the waterbody, followed by contacting at least one flocculant(s) with said waterbody in one or more dosages and subjecting to further mixing for a predetermined time period;
  b. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to living organism and non-living matter.

In a non-limiting embodiment, the present disclosure provides for a method of combining chemicals including but not limiting to coagulant(s) and flocculant(s) for separation of solid particles, including but not limiting to living organisms and non-living matter, from a waterbody including but not limiting to fresh water and marine water by coagulation and flocculation, wherein said method comprises non-limiting acts of—
  a. contacting first coagulant(s) with the waterbody in one or more dosages and mixing the waterbody, followed by subjecting the waterbody to contacting with second coagulant(s);
  b. further mixing the waterbody for a predetermined time period and contacting the waterbody with flocculant(s), followed by mixing;
  c. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to living organism and non-living matter.

In an exemplary embodiment, the present disclosure provides for a method of combining chemicals including but not limiting to coagulant(s) and flocculant(s) for separation of living organism including but not limiting to algae from a waterbody including but not limiting to fresh water and marine water by coagulation and flocculation, wherein said method comprises acts of:
  a. contacting at least one coagulant (s) with the waterbody in one or more dosages, and mixing the waterbody, followed by contacting at least one flocculant (s) with said waterbody in one or more dosages and subjecting to further mixing for a predetermined time period;
  b. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the living organism including but not limiting to algae.

In a non-limiting embodiment, the above described methods of the present disclosure include mixing of waterbody with chemicals including but not limiting to coagulant(s) and flocculant(s), wherein single or multiple dosage of chemicals are added. Such mixing is carried out by any known or conventional technique that a person of average skill in the art deems fit. The said mixing is carried out for predetermined duration and at predetermined speed. For organisms including living organisms such as algae, preferably, the duration ranges from about 10 seconds to about 10 minutes, and the speed of said mixing ranges from about 40 rpm to about 400 rpm.

In another non-limiting embodiment, duration and speed of mixing in the above described methods may be determined by and/or depended on presence or absence of optional process which include but are not limited to air flotation such as dissolved air flotation, froth flotation and/or filtration through mesh and/or membranes, wherein these process(s) are optionally employed in the instant method for efficient separation of said solid particles, including but not limiting to living organisms and non-living matter.

Figure 1:
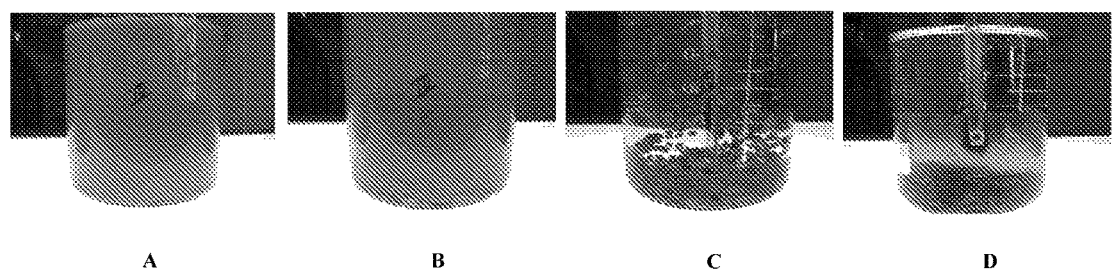

In an exemplary embodiment, FIG. 1 illustrates the action of coagulant(s) and flocculant(s) combination during solid particle separation from a waterbody by the methods of the present disclosure, wherein A) represents waterbody comprising said solid particles; B) represents pin flock formation after addition of coagulant(s); C) represents aggregation of pin flocks to form larger flocks after addition of flocculant(s); and D) represents settled flock of solid particles after stirring is stopped.

The unique combination of coagulant(s) and flocculant(s) in the methods of the present disclosure destabilizes the stable solid particles including but not limiting to living organisms and non-living matter, and leads to a formation of large flocks resulting in rapid separation of said solid particles from a waterbody including but not limiting to fresh water or marine water.

In an alternate embodiment, the coagulant(s) employed in the methods of the present disclosure destabilizes the solid particles resulting in the formation of pin flocks, which facilitates the formation of large flocks.

In another embodiment, the unique combination of coagulant(s) and flocculant(s) in the method of the present disclosure destabilizes the stable living organism such as algae and/or bacteria in the waterbody and leads to formation of large flocks of algae and/or bacteria resulting in rapid separation of living organism such as algae and/or bacteria from a waterbody including but not limiting to fresh water or marine water.

In an alternate embodiment, the coagulant(s) employed in the methods of the present disclosure destabilizes living organism such as algae and/or bacteria in the waterbody resulting in the formation of pin flocks, which facilitates the formation of large flocks of algae and/or bacteria in the waterbody, aiding in the separation of said living organism such as algae and/or bacteria.

In a non-limiting embodiment, the strongly cationic medium or low molecular weight, short chain coagulant(s) employed in the methods of the present disclosure neutralizes the negative surface charge of the solid particles in the waterbody, preferably living organisms such as algae and/or bacteria, by imparting a slight positive surface charge to said solid particles. Neutralization of the surface charge drastically reduces the mutual repulsion between the solid particles, causing destabilization which results in the formation of pin flock or coagula. Addition of strongly anionic high molecular weight, long chain flocculant(s) to the destabilized solid particles, attracts the slight positive charge of the destabilized solid particles resulting in the formation of large flock, which ranges in the size of few millimeters to centimeters. The effectiveness of flocculant(s) in the above described method is thus dependent on the formation of pin flocks, which is in turn dependent on the efficiency of the coagulant(s). The flocculant(s) will have absolutely no effect if added to a waterbody for separation of such solid particles, including but not limiting to living organisms such as algae and/or bacteria, before addition of sufficient amount of coagulant(s), as the coagulant(s) breaks the stability of the said solid particles.

In a non-limiting embodiment of any of the above described methods, varied concentration of chemicals including but not limiting to coagulant(s) and flocculant(s) are required for separation of solid particles including but not limiting to living organism such as algae and bacteria, which are either microscopic or macroscopic in nature, from a waterbody including but not limiting to fresh waterbody or marine water. The concentration of said coagulant is dependent on the concentration of said solid particles such as algae and/or bacteria in the waterbody, wherein relationship between the coagulant(s) and concentration of the solid particles is logarithmic, and wherein higher the concentration, the easier and lower is the total dosage of chemicals per unit biomass of the solid particles including such as algae and/or bacteria.

In an exemplary embodiment, parameters that affect coagulant dosage in any of the above described non-limiting methods include but are not limited to pH, salinity, extracellular organic matter, natural organic matter, particle size, particle concentration, surface charge density and particle type or a combination thereof.

In an exemplary embodiment, effectiveness of any of the above described methods is determined by parameters including but not limiting to coagulant and flocculant dosage, sequence of addition of coagulant and flocculant, period of incubation/mixing and mixing speed, or a combination thereof.

In an exemplary embodiment, the flocks of solid particles such as algae and/or bacteria upon addition of coagulants and flocculants are recovered either by allowing it to settle under gravity in a settling tank or floating it out by attaching micro-bubbles to their surface using a dissolved air flotation. Further, one skilled in the art would be aware that the formed flocks of said solid particles can be recovered by employing various conventional physical and chemical processes without compromising on the yield of the recovery of said solid particles.

In an alternative embodiment of the present disclosure, the above described methods of separating solid particles by employing the unique combination of chemicals including but not limiting to coagulant(s) and flocculant(s) of present disclosure through a process of coagulation and flocculation is combined with methods including but not limiting to electro-coagulation and pH modulation or a combination thereof.

In an alternative embodiment of the present disclosure, the described coagulation and flocculation in the method of the present disclosure is combined with electro-coagulation, wherein the electro-coagulation involves supply of power or electrical current into the waterbody comprising solid particles, including but not limiting to living organisms such as algae and/or bacteria, followed by employing the unique combination of chemicals including but not limiting to coagulant(s) and flocculant(s) of the present disclosure. The said combination of electro-coagulation with the chemical coagulation and flocculation of the present disclosure is referred to herein as 'hybrid electro-coagulation'. During electrocoagulation, the electric current is supplied into the waterbody by a set of electrodes, when the power (by battery or any other power source) is applied it results in liberation of metal cations from the electrodes into the algae suspension which results in coagulation of algae in the waterbody by neutralizing algae surface charge.

In an embodiment, the metals employed as electrodes have certain electrode potential and the applied voltage must be above this electrode potential, which is metal specific such that the metal ion is liberated. Therefore, the applied voltage is generally about 10% above the electrode potential of a given metal being used for electrocoagulation.

Figure 6:
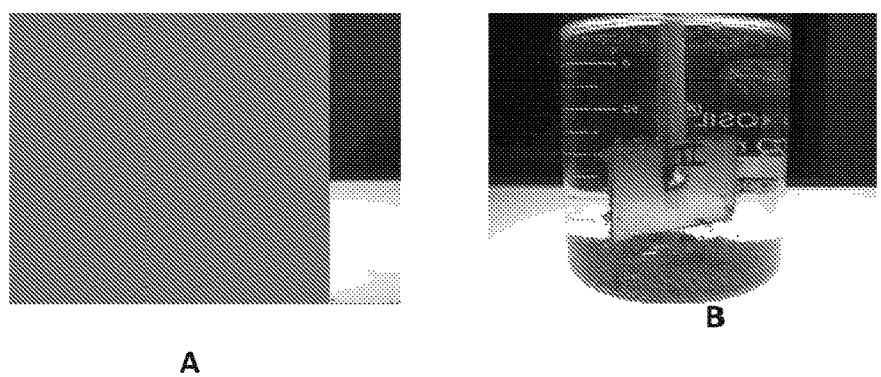
FIG. 6 illustrates the degree of settling of solid particles achieved upon employing hybrid electro-coagulation approach.

In a preferred embodiment, the electrical current in the hybrid electro-coagulation approach destabilizes the solid particles including but not limiting to living organisms such as algae and/or bacteria, which is to be separated from a waterbody including but not limiting to fresh water and marine water, followed by addition of the unique combination of coagulant(s) and flocculant(s) of the present disclosure. The electro-coagulation is an electrochemical method which involves responses of the said solid particles on the waterbody to electric fields and electrically induced oxidation and reduction reaction where sacrificial anodes corrode to release into solution, active coagulant precursors including but not limiting to aluminium, iron and copper are employed depending on the type of electrode used. At the cathode, gas evolves (usually as hydrogen bubbles) accompanying electrolytic reactions. This therefore causes destabilization of the said solid particles such as algae and/or bacteria and aggregation of smaller particles into larger particles. FIG. 6 illustrates the degree of settling achieved upon employing hybrid electro-coagulation approach while separating solid particles from a waterbody.

Figure 4:
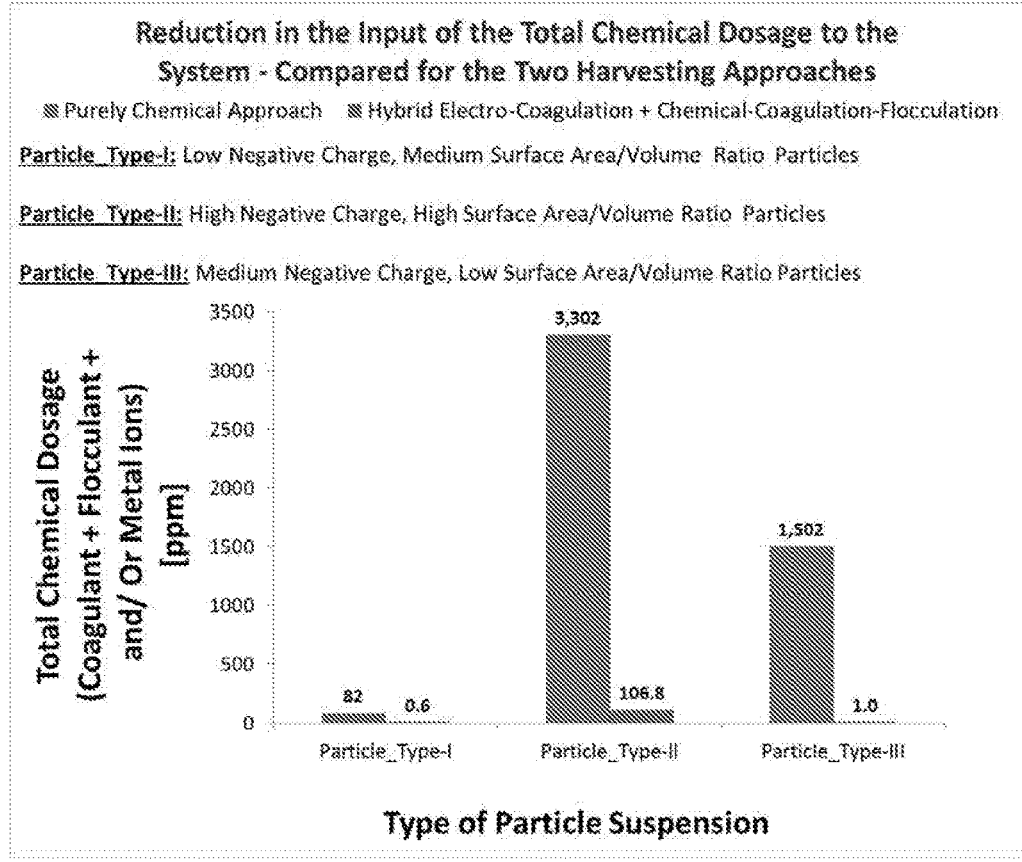
FIG. 4 illustrates the total dosage of coagulant and flocculant that may be employed in purely chemical approach and hybrid Electro-coagulation-Chemical-Coagulation-Flocculation approach with metal ions.

In an exemplary embodiment, the hybrid electro-coagulation results in significant reduction of coagulant dosage when compared to the process of chemically separating the solid particles by only using the unique combination of coagulant(s) and flocculant(s). FIG. 4 provides consumption of coagulant and flocculant in hybrid electro-coagulation in comparison to pure chemical approach of coagulation-flocculation, for separation of solid particles, including but not limiting to living organisms. The illustration is with respect to different possible types of solid particles. For example, the solid particles are of three different types, i.e., type-I, type-II and type-III. The type-I solid particles is low negative charge with medium surface area per volume ratio particles; type-II solid particles is high negative charge with high surface area per volume ratio particles; and type-III solid particles is medium negative charge with low surface area per volume ratio particles. As can be seen from FIG. 4, the Total chemical dosage required in hybrid electro-coagulation has significantly reduced when compared to the purely chemical separation of solid particles, Table 1 below illustrates the reduction in the Total chemical dosage hybrid Electro-coagulation (Coagulant+Flocculant+Metal Ion) when compared to in purely chemical approach (Coagulant+Flocculant). Further table 2 below illustrates the cost that is involved in purely chemical approach and hybrid electro-coagulation.

TABLE 1 illustrates the amount of Total chemical dosage in purely chemical approach vis-à-vis hybrid electro-coagulation.

|   | Purely Chemical Approach Total [Coagulant + Flocculant] Dosage ppm | Hybrid Electro-Coagulation + Chemical-Coagulation-Flocculation Total [Coagulant + Flocculant + Metal Ion] Dosage ppm |
| --- | --- | --- |
| Particle_Type-I | 82.00 | 0.6 |
| Particle_Type-II | 3302.00 | 106.8 |
| Particle_Type-III | 1502.00 | 1.0 |

TABLE 2 illustrates the cost involved for purely chemical approach vis-à-vis hybrid electro-coagulation.

|   | Purely Chemical Approach Total Cost of Coagulant + Flocculant ($/m3 of Suspension) | Hybrid Electro-Coagulation + Chemical-Coagulation-Flocculation Total Cost of Coagulant + Flocculant + Metal Ions ($/m3 of Suspension) |
| --- | --- | --- |
| Particle_Type-I | 0.08 | 0.001576286 |
| Particle_Type-II | 3.30 | 0.133243137 |
| Particle_Type-III | 1.50 | 0.005898616 |

The illustrations also suggest that the trend is almost similar for different types of particles. Although, the relative difference in the performance of hybrid electro-coagulation approach in comparison to chemical coagulation-flocculation approach would remain similar for different particle types, the absolute dosages or current to be passed would differ based on the property of the waterbody having the solid particles.

Figure 5:
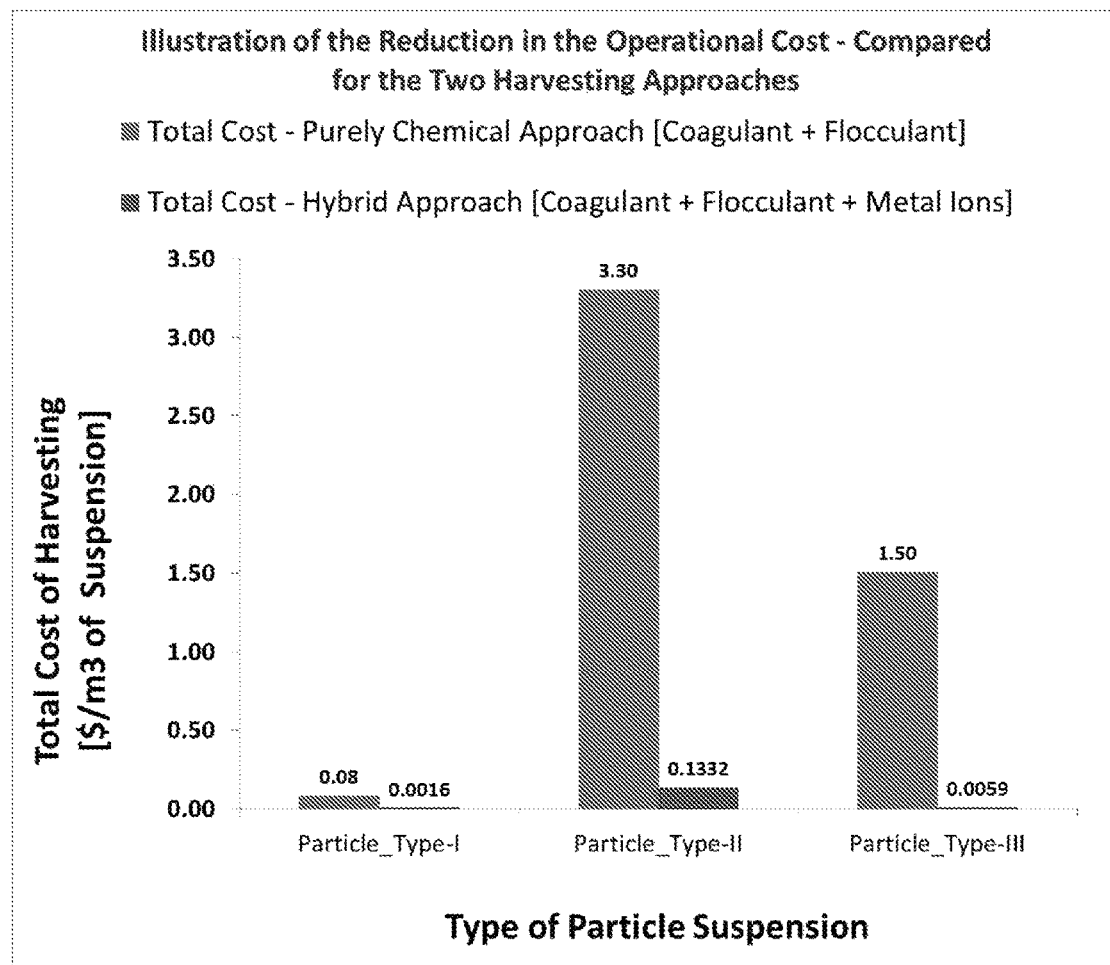
FIG. 5 illustrates the possible cost involved upon employing coagulant-flocculant approach and hybrid electro-coagulation approach.

In an exemplary embodiment, the hybrid electro-coagulation is cheaper than the conventional chemical approach of separating solid particles. The hybrid electro-coagulation also plays a vital role in reducing the cost involved in separating the solid particles, including but not limiting to living organisms such as algae and bacteria from a waterbody. FIG. 5 illustrates the analysis of cost for separating solid particles from a waterbody including but not limiting to fresh water and marine water, upon employing hybrid electro-coagulation and chemical approach of coagulation-flocculation. The said illustration is with respect to different possible types of solid particles. For example, the solid particles are of three different types, i.e., type-I, type-II and type-III. The type-I solid particles is low negative charge with medium surface area per volume ratio particle; type-II solid particles is high negative charge with high surface area per volume ratio particle; and type-III solid particles is medium negative charge with low surface area per volume ratio particle. As can be seen from these illustrations, the cost for employing hybrid electro-coagulation has significantly reduced when compared to the purely chemical separation of solid particles. The illustrations also suggest that the trend is almost similar regardless of different types of particles. In other words, the relative grading of reduction in the cost that is observed will be similar when the method is employed for separation of any type of algae and/or bacteria. And, a skilled person would be aware that the absolute value of the reduction in cost is a specific function of the cell type and the specific properties of the waterbody having solid particles such as algae and/or bacteria.

In another embodiment, the hybrid electro-coagulation has a positive impact on the waterbody recyclability of the spent medium due to the reduction in the addition of chemicals in to the waterbody during separation of solid particles, including but not limiting to living organisms such as algae and/or bacteria.

In another embodiment, the hybrid electro-coagulation is simple, efficient, fast, easily deployable and clean and most importantly results in a high degree of settling of the solid particles including but not limiting to living organism such as algae and/or bacteria and thereby enhancing the recovery of said solid particles.

In an exemplary embodiment, the present disclosure relates to a method of separating solid particles, including but not limiting to living organisms from a waterbody such as fresh water and/or marine water waterbody by employing electro-coagulation followed by unique combination of chemicals including but not limiting to coagulant(s) and flocculant(s) of present disclosure through a process of coagulation and flocculation, wherein the said combination in the said method comprises single dosage or multiple dosage of coagulant(s) and flocculant(s).

In a non-limiting embodiment, the instant method provides employing current and combining the chemicals including but not limiting to coagulant(s) and flocculants(s) in any sequence and for any time period thereof within the scope of this disclosure. Said process of combining of chemicals including but not limiting to coagulant(s) and flocculants(s) and electric current provides separation of said solid particles from waterbody including but not limiting to fresh water and marine water, through a process of chemical coagulation and chemical flocculation and electro-coagulation and involves plurality of coagulant(s) and/or flocculants(s).

In a non-limiting embodiment, the present disclosure provides for a method of electro-coagulation followed by coagulation and flocculation for separation of solid particles including but not limiting to living organisms such as algae and/or bacteria, from a waterbody including but not limiting to fresh water and marine water, wherein said method comprises non-limiting acts of— a. contacting electric current with the waterbody
b. contacting at least one coagulant(s) with the waterbody of step (a) in one or more dosages, and mixing the waterbody, followed by contacting at least one flocculant(s) with said waterbody and subjecting to further mixing;
c. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to living organism such as algae and/or bacteria.

In a non-limiting embodiment, the present disclosure provides for a method of electro-coagulation followed by coagulation and flocculation for separation of solid particles including but not limiting to living organisms such as algae and/or bacteria, from a waterbody including but not limiting to fresh water and marine water, wherein said method comprises non-limiting acts of— a. contacting electric current with the waterbody;
b. contacting first coagulant(s) with the waterbody of step (a) in one or more dosages, and mixing the waterbody followed by subjecting the mixed waterbody to contacting with second coagulant(s);
c. further mixing the waterbody and subjecting said waterbody to contacting with flocculant(s) and mixing;
d. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to living organism such as algae and/or bacteria.

In a non-limiting embodiment, the above described methods of the present disclosure after electro-coagulation include mixing of waterbody with chemicals including but not limiting to coagulant(s) and flocculant(s), wherein single or multiple dosage of chemicals are added. Such mixing is carried out by any known or conventional technique that a person of average skill in the art deems fit. The said mixing is carried out for predetermined duration and at predetermined speed. For organisms including living organisms such as algae and/or bacteria, preferably, the duration ranges from about 10 seconds to about 10 minutes, and the speed of said mixing ranges from about 40 rpm to about 400 rpm.

In another non-limiting embodiment, duration and speed of mixing in the above described methods may be determined by and/or may be dependent on presence or absence of optional process which include but are not limited to air flotation such as dissolved air flotation, froth flotation and/or filtration through mesh and/or membranes, wherein these process(s) are optionally employed in the instant method for efficient separation of said solid particles including but not limiting to living organisms such as algae and/or bacteria.

In another non-limiting embodiment, the instant disclosure provides a set-up for performing said hybrid electro-coagulation, wherein the said set-up is in configurations including but not limiting to in-situ configuration and continuous harvesting configuration.

Figure 7:
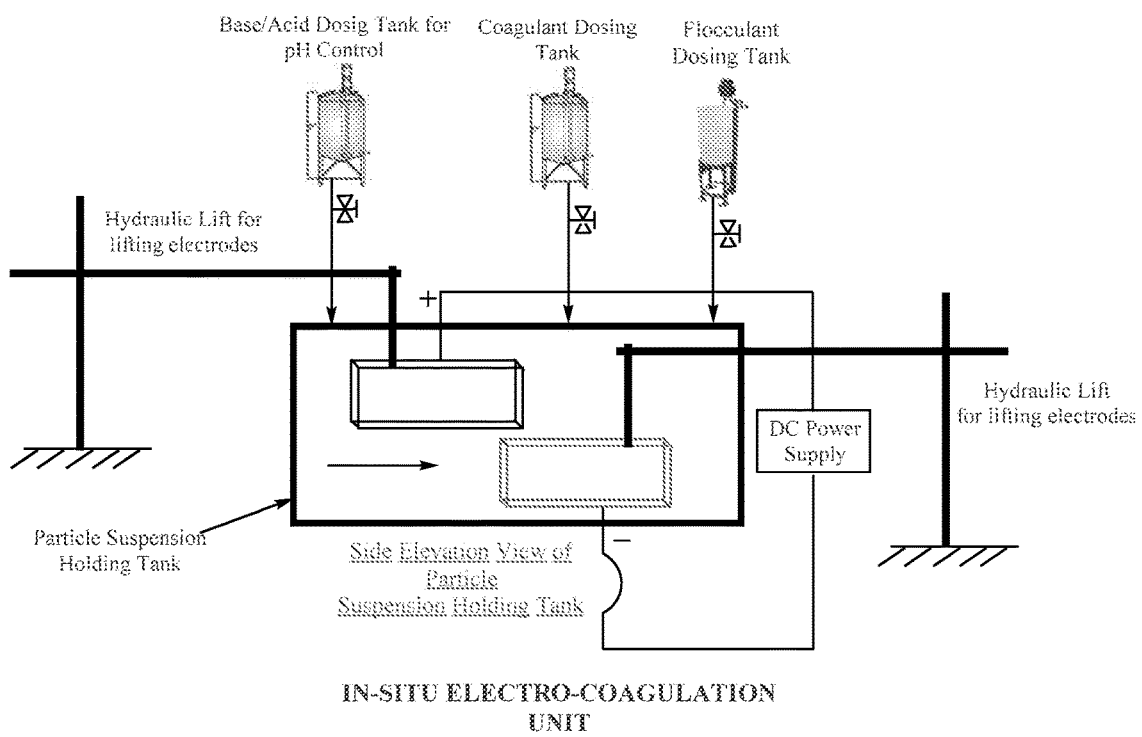
FIG. 7 illustrates the in-situ configuration for hybrid electro-coagulation and coagulation-flocculation approach.

In a preferred embodiment, FIG. 7 illustrates the in-situ configuration, wherein the in-situ configuration comprises components including but not limiting to (1) set (s) of electrodes of suitable MOC for affecting electro-coagulation, (2) retractable hydraulic or mechanical arms to mount the electrodes, to immerse and remove the electrodes from the vessel and (3) a DC/AC power supply for providing the necessary power source to affect electro-coagulation. The setup also includes a coagulant and flocculant dosing tank, acid/base dosing tank for pH adjustment, pumps and the requisite accessories for the same (4). In this configuration the electrode plates are mounted on retractable hydraulic arms which retract during normal cultivation of solid particles, and can be deployed in to the waterbody when separating is to be conducted, wherein the said in-situ configuration is suitable for both small scale and large scale separation of solid particles including but not limiting to living organisms such as algae and/or bacteria. In the said in-situ harvesting the water will not have to be pumped to a central processing or harvesting facility for separation of solids from liquid which will result in significant cost saving related to pumping of water to and fro. Water pumping costs are very high and could make or break process. In-situ process enables unique methods of separating the solids from liquids within the waterbody without the need for transporting the water from different algal cultivation ponds to a centralized facility.

Figure 8:
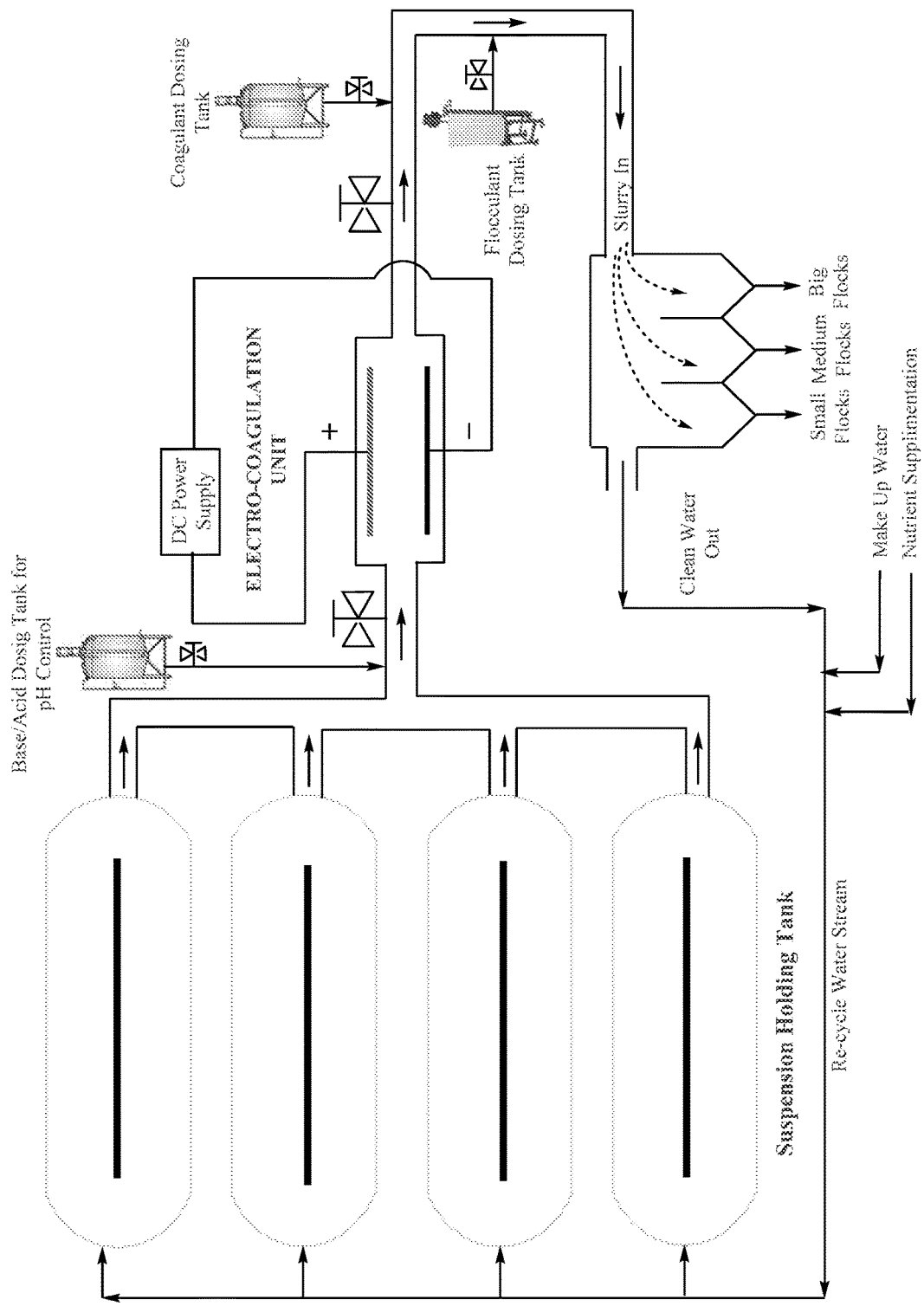
FIG. 8 illustrates the continuous harvesting configuration for hybrid electro-coagulation and coagulation-flocculation approach.

In another preferred embodiment, FIG. 8 illustrates the continuous harvesting configuration, wherein said continuous harvesting configuration comprises components including but not limiting to (1) set(s) of electrodes of suitable MOC for affecting Electro-coagulation, (2) retractable hydraulic or mechanical arms to mount the electrodes, to immerse and remove the electrodes from the vessel and (3) a DC/AC power supply for providing necessary power source to affect electro-coagulation. The setup also includes a coagulant and flocculant dosing tank, acid/base dosing tank for pH adjustment, pumps and the requisite accessories for the same (4), set of pumps/pumping station to pump all the fluid to the electro-coagulation unit (5) and a segmented settling tank (6) which is suitable for continuous operation and for large quantity of culture condition.

In another alternative embodiment of the present disclosure, the described method comprising coagulation-flocculation is combined with pH modulation, wherein pH of the waterbody comprising solid particles including but not limiting to living organisms such as algae and/or bacteria; is varied upon addition of acid or base, wherein the base is selected from a group comprising sodium hydroxide (NaOH) and potassium hydroxide (KOH), or a combination thereof and wherein the acid is selected from a group comprising hydrochloric acid, nitric acid and sulphuric acid, or any combination thereof, followed by addition of the unique combination of chemicals including but not limiting to coagulant(s) and flocculant(s) of the instant disclosure. The said method of coagulation-flocculation combined with pH modulation is referred herein as 'pH modulated coagulation-flocculation'.

Figure 2:
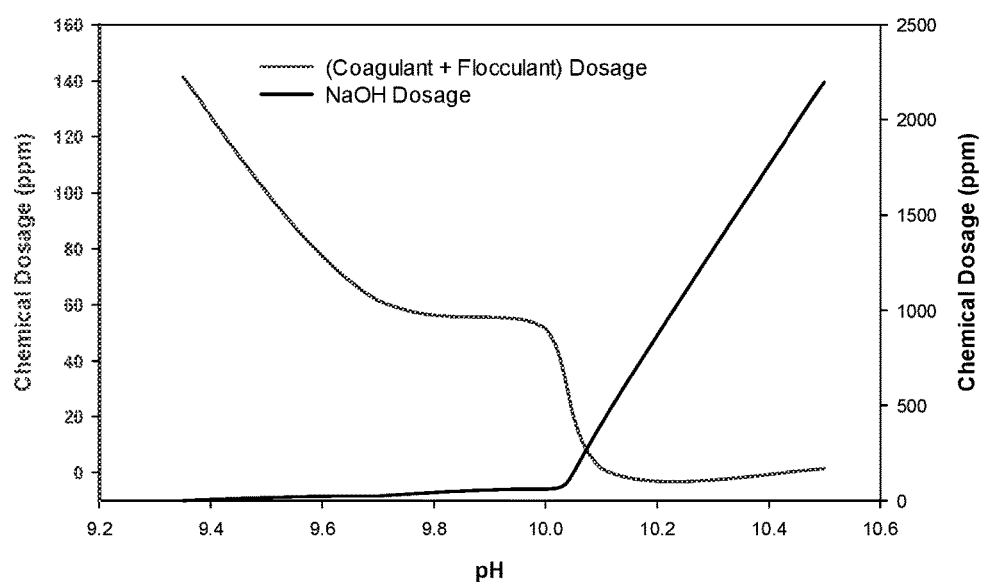
FIG. 2 illustrates a pattern of dosage of chemicals in pH modulated chemical coagulation and flocculation approach during separation of solid particles.
Figure 3:
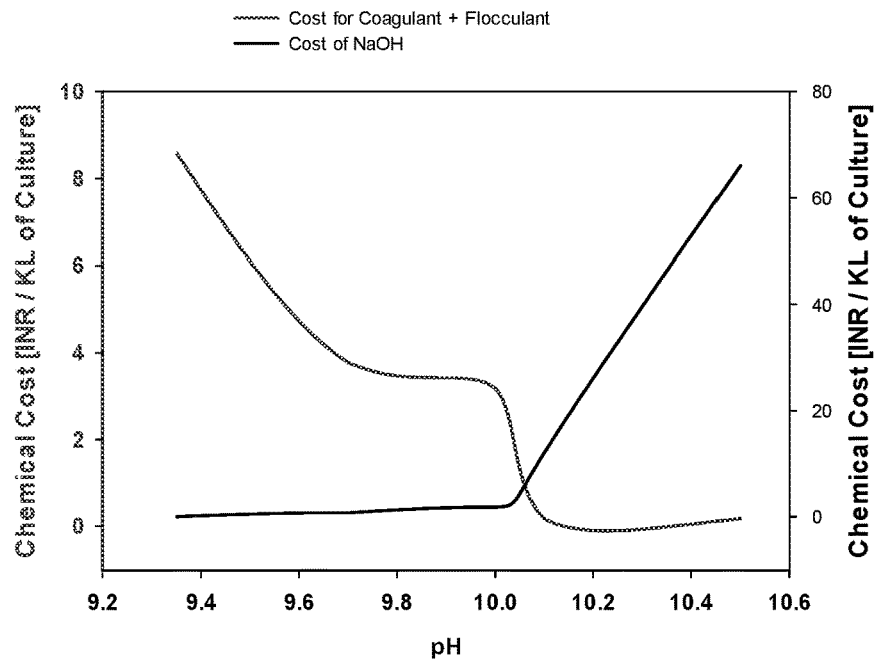
FIG. 3 illustrates a cost analysis pattern of chemicals dosed during separation of solid particles in pH modulated chemical coagulation-flocculation approach.

In an exemplary embodiment, the method comprising the step of pH modulated coagulation-flocculation reduces the chemical dosage of coagulant(s) and flocculant(s) by about 2 to about 3 folds when compared to a method employing only unique combination of coagulant(s) and flocculant(s). FIG. 2 provides for a pattern of coagulant and flocculant dosage in pH modulated coagulation-flocculation in comparison to coagulation-flocculation approach and pH induced flocculation approach individually. Further, FIG. 3 illustrates the cost analysis upon employing pH modulated coagulation-flocculation approach for separating solid particles from a waterbody including but not limiting to fresh water and marine water, when compared to coagulation-flocculation approach and pH induced flocculation approach individually for said separation of solid particles.

In an exemplary embodiment, the coagulant dosage upon employing the pH modulated coagulation-flocculation approach is reduced significantly when compared to only using the unique combination of coagulant(s) and flocculant(s).

In an exemplary embodiment, the percentage recovery of said solid particles including but not limiting to living organisms such as algae and/or bacteria from a waterbody upon employing pH modulated coagulation-flocculation approach of the present disclosure is at least 95%.

In an exemplary embodiment, the present disclosure relates to a method of separating solid particles including but not limiting to living organisms from a waterbody such as fresh water and marine water by employing pH modulation followed by unique combination of chemicals including but not limiting to coagulant(s) and flocculant(s) of present disclosure through a process of coagulation and flocculation, wherein the said combination in the said method comprises single dosage or multiple dosage of coagulant(s) and flocculant(s), respectively.

In a non-limiting embodiment, the instant method provides for modulating pH and combining the chemicals including but not limiting to coagulant(s) and flocculants(s) in any sequence and for any time period thereof within the scope of this disclosure. Said process of combining of chemicals including but not limiting to coagulant(s) and flocculants(s) and pH modulation provides separation of solid particles including but not limiting to living organism such as algae and/or bacteria from waterbody including but not limiting to fresh water and marine water, through process of chemical coagulation and chemical flocculation and pH modulation and involves plurality of coagulant(s) and/or flocculants(s).

In a non-limiting embodiment, the present disclosure provides for a method of pH modulation followed by coagulation and flocculation for separation of solid particles including but not limiting to living organisms such as algae and/or bacteria from a waterbody including but not limiting to fresh water and marine water, wherein said method comprises acts of—
 a. modulating pH of the waterbody;
 b. contacting at least one coagulant(s) with the waterbody of step (a) in one or more dosages, and mixing the waterbody, followed by contacting at least one flocculant(s) with said waterbody and subjecting to further mixing;
 c. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to algae and/or bacteria.

In a non-limiting embodiment, the present disclosure provides for a method of pH modulation followed by coagulation and flocculation for separation of solid particles including but not limiting to living organisms such as algae and/or bacteria, from a waterbody including but not limiting to fresh water and marine water, wherein said method comprises acts of—
 a. modulating pH of the waterbody;
 b. contacting first coagulant(s) with the waterbody of step (a) in one or more dosages, and mixing the waterbody followed by subjecting the mixed waterbody to contacting with second coagulant(s);
 c. further mixing the waterbody and subjecting said waterbody to contacting with flocculant(s) and mixing;
 d. reducing or stopping the mixing and allowing the waterbody to settle post the mixing or optionally subjecting the waterbody to a process including but not limiting to air flotation such as dissolved air flotation, froth flotation and/or filtration through mesh and/or membranes for efficient separation of the solid particles including but not limiting to living organism such as algae and/or bacteria.

In a non-limiting embodiment, the above described pH modulated coagulation-flocculation methods of the present disclosure include a mixing of waterbody with chemicals including but not limiting to coagulant(s) and flocculant(s), wherein single or multiple dosage of chemicals are added. Such mixing is carried out by any known or conventional technique that a person of average skill in the art deems fit. The said mixing is carried out for predetermined duration and at predetermined speed. For organisms including living organisms such as algae and/or bacteria, preferably, the duration ranges from about 10 seconds to about 10 minutes, and the speed of said mixing ranges from about 40 rpm to about 400 rpm.

In another non-limiting embodiment, duration and speed of mixing in the above described pH modulated coagulation-flocculation methods may be determined by and/or depended on presence or absence of optional process which include but are not limited to air flotation such as dissolved air flotation, froth flotation and/or filtration through mesh and/or membranes, wherein these process(s) are optionally employed in the instant method for efficient separation of said solid particles including but not limiting to living organisms such as algae and/or bacteria.

In an embodiment of the present disclosure during pH modulated coagulation and flocculation approach, addition of base such as sodium hydroxide and/or potassium hydroxide or addition of acid such as hydrochloric acid, nitric acid or sulphuric acid to the waterbody having solid particles including but not limiting to living organisms such as algae and/or bacteria, for pH modulation, causes coagulation of algae and/or bacteria.

In yet another alternative embodiment of the present disclosure, the above described methods of separating solid particles including but not limiting to living organism such as algae and/or bacteria by employing the unique combination of chemicals including but not limiting to coagulant(s) and flocculant(s) of present disclosure through a process of coagulation and flocculation is combined with both electro-coagulation and pH modulation techniques as described in the disclosure. The processes of pH modulation, electrical conduction and combination of said chemicals in the instant method are employed in either a predetermined sequence or in any order thereof within the scope of this disclosure.

In an embodiment, the advantages combining unique combination of chemicals including but not limiting to coagulant and flocculant in combination with electro-coagulation and pH modulation techniques over other individual techniques are— pH adjustment to acidic or alkaline aids in significantly reduce the chemical coagulant dosage required for harvesting;

addition of extremely low concentration of high molecular weight polymers (flocculant) significantly enhances the rate of settling post coagulation in this way the unique method significantly reduces the overall time required for solid (algae and/or bacteria)-liquid separation;

the combination of chemical coagulation chemical flocculation, electro-coagulation and pH modulation techniques in any sequence or order leads to lowest chemical input to the system which has several advantages such as lowest cost and lowest environmental impact;

In another alternate embodiment, the present disclosure the method of separation solid particles including but not limiting to living organism such as algae and/or bacteria comprises a step of combining pH modulation and electro-coagulation, wherein the pH of the waterbody having the algae and/or bacteria is modulated by addition of base including but not limiting to sodium hydroxide and/or potassium hydroxide or addition of acid including but not limiting to hydrochloric acid, nitric acid or sulphuric acid, followed by contacting the waterbody with electric current, wherein the electrodes releases metal cations causing coagulation of the algae and/or bacteria and adding flocculant. In an embodiment of the present disclosure, during pH modulation of the waterbody having algae and/or bacteria, coagulation of algae and/or bacteria occurs.

In an embodiment, FIG. 1 in the present disclosure illustrates the action of coagulant(s) and flocculant(s) combination on a waterbody comprising solid particles, wherein A) represents waterbody comprising said solid particles; B) represents pin flock formation after addition of coagulant(s); C) represents aggregation of pin flocks to form larger flocks after addition of flocculant(s); and D) represents settled flock of solid particles after stirring is stopped.

In an embodiment, FIG. 2 in the present disclosure illustrates a pattern of dosage of chemicals in pH modulated chemical coagulation and flocculation approach during separation of solid particles.

In an embodiment, FIG. 3 in the present disclosure illustrates a pattern of chemicals dosed during separation of solid particles in pH modulated chemical coagulation-flocculation approach.

In an embodiment, FIG. 4 in the present disclosure illustrates the total dosage of coagulant and flocculant that may be employed in purely chemical approach and hybrid Electro-coagulation-chemical coagulation and flocculation approach, wherein passing electric current for electro-coagulation releases metal ions.

In an embodiment, FIG. 5 in the present disclosure illustrates the possible cost involved upon employing coagulant-flocculant approach and hybrid electro-coagulation approach.

In an embodiment, FIG. 6 in the present disclosure illustrates the degree of settling of solid particles achieved upon employing hybrid electro-coagulation approach.

In an embodiment, FIG. 7 in the present disclosure illustrates the in-situ configuration for hybrid electro-coagulation and coagulation flocculation approach.

In an embodiment, FIG. 8 in the present disclosure illustrates the continuous harvesting configuration for hybrid electro-coagulation and coagulation-flocculation approach.

In an embodiment, FIG. 9 in the present disclosure illustrates comparison of the operating cost (OPEX) for the methods such as chemical coagulation (Case-E), chemical coagulation and chemical flocculation (Case-A), pH modulated coagulation and flocculation (Case-B), electro-coagulation and chemical flocculation (Case-D), pH modulation, electro-coagulation and chemical coagulation and flocculation (Case-C4) and Chemical flocculation (Case-F), for separation of bacteria such as *E. coli* from a waterbody such as fresh water.

In another embodiment, FIG. 10 in the present disclosure illustrates comparison of the operating cost (OPEX) for separation of algal species such as *Picochlorum* sp by techniques such as chemical coagulation, chemical coagulation and chemical flocculation, pH modulated coagulation and flocculation, electro-coagulation and chemical flocculation, pH modulation, electro-coagulation and chemical coagulation and flocculation and Chemical flocculation.

In another embodiment, FIG. 11 in the present disclosure illustrates biomass normalized coagulant dosage required for 95% algae separation as a function of algal species and parameters. The figure illustrates separation of algal species such as *Scenedesmus* sp, *Cyanobacterium aponium*, *Nannochloropsis* sp, *Pseudooneochloris* sp, *Picochlorum* sp, *Nanochloropsis oceanica* and separation of consortia of algal species.

In another embodiment, FIG. 12 in the present disclosure illustrates the effect of medium salinity measured in terms of sodium chloride (NaCl) and sea salts on coagulant dosage required for achieving 95% cell recovery/harvesting for *Nannochloropsis* sp.

In another embodiment, FIG. 13 in the present disclosure illustrates the effect of medium salinity measured in terms of sodium chloride (NaCl) and sea salts on coagulant dosage required for achieving 95% cell recovery/harvesting for *Picochlorum* sp. Coagulant dosage is reported after normalized with biomass harvested as dry cell weight (DCW)

In another embodiment, FIG. 14 in the present disclosure illustrates medium pH on coagulant dosage required for achieving 95% cell recovery/harvesting for *Picochlorum* sp. Coagulant dosage is reported after normalized with biomass harvested as dry cell weight (DCW).

In another embodiment, FIG. 15 in the present disclosure illustrates the effect of cell concentration on coagulation efficiency in the electrocoagulation for achieving 95% cell recovery for *Nannochloropsis* sp, *Nannochloropsis oceanica* and consortia of algal species. Dosage is reported after normalized with biomass harvested as dry cell weight (DCW). The data in the FIG. 15 demonstrates that increase in the cell concentration decreases the metal discharge required per unit biomass harvested.

In another embodiment, FIG. 16 in the present disclosure illustrates the effect of cell concentration on coagulation in chemical coagulation and chemical flocculation for achieving 95% cell recovery for *Nannochloropsis* sp and consortia of algal species. Dosage is reported after normalized with biomass harvested as dry cell weight (DCW). The data in the FIG. 16 demonstrates that increase in the cell concentration decreases the coagulant dosage required per unit biomass harvested.

In another embodiment, FIG. 17 in the present disclosure illustrates effect of usage of two coagulants vis-à-vis one coagulant in the methods of the instant disclosure. From FIG. 17 it can be understood that when two coagulants are employed in the methods of the present disclosure the amount of chemical (coagulant) required for separation of living organisms including but not limiting to algae and bacteria is reduced when compared to use of one coagulant in the methods of the present disclosure for separation of living organism including but not limiting to algae and bacteria.

In another embodiment, the duration of separation of algae and/or bacteria by the methods of the present disclosure is about 5 minutes, whereas the duration of separation of algae and/or bacteria by the conventional methods such as— entriguation is 10 minutes to 20 minutes;
unaided sedimentation is 1 day to 3 days;
flotation is 10 minutes to 20 minutes; and
filtration is 10 minutes to 15 minutes.

In an embodiment of the present disclosure, below is the list of algae employed in the instant disclosure for demonstrating the effectiveness of the methods of the instant disclosure. However, the effect of the methods of the instant disclosure is not limited to only these algae, but is applicable to all types of algae, bacteria and other microscopic organism.

| Scientific Name of Algae | Source and Geographical origin |
| --- | --- |
| Scenedesmus sp. | Patalganga, Khalapur, Raigad |
| Cyanobacterium aponinum | Gagva |
| Nannochloropsis Sp. | Kashid, Maharastra, |
| Nannochloris sp. | Bhayander, maharashtra, |
| Pseudoneochloris sp. | Anjuna, Goa |
| Picochlorum sp. | Alibag, Maharashtra |
| Nannochloropsis oceanica | Gagva |
| Nanochloropsis sp. | Gagva |
| Chlorella sorokiniana | Gagva |
| Chlorella vulgaris | Jamnagar |
| Nannochlorum sp. | Jamnagar |

In another embodiment, the methods of the instant disclosure demonstrates effectiveness the effectiveness of the methods of the instant disclosure in separation of organisms such as Marine or Sea Water Algae selected from a group comprising Dunaliella bioculata; Dunaliella salina; Prymnesium parvum; Tetraselmis maculate Porphyridium cruentum; Synechoccus sp. Spirulina; Haematococcus; Cyanophyceae; Chlorophyceae; Bacillariophyceae and Chrysophyceae;
macro algae including but not limiting to Alaria; Corallina; Cystoseira; Ecklonia and Eucheumia;
fresh water algae including but not limiting to Scenedesmus obliquus; Scenedesmus quadricauda; Scenedesmus dimorphus Chlamydomonas rheinhardii; Chlorella vulgaris; Chlorella pyrenoidosa; Spirogyra sp.; Euglena gracilis; Spirulina platensis; Spirulina maxima; Anabaena cylindrical and Aphanizomenon flos-aquae; and bacteria including but not limiting to Lacto bacilli; Streptomyces; Bacillus; actinomycetous bacteria; Lactococcus Lactis; Spirochaeta; Aquaspirillum Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. The examples provided herein are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLE

Example-1: Demonstrates Reduction in Chemical Dosage by Unique Combination of Coagulant and Flocculant A waterbody comprising solid particles such as microorganisms (e.g., an algal culture) is treated with the combinatorial dose of coagulant and flocculant as described in the instant disclosure for harvesting or separation of said microorganism from the waterbody and results in a reduced dosage of coagulant. Initially a cationic coagulant at a rate of about 5 ppm to 500 ppm for 500 ppm to 5000 ppm of microorganism in the waterbody, thereby destabilizing the microorganism suspension to form pin flocks by virtue of charge neutralization. Thereafter an anionic flocculant at a rate of about 0.5 ppm to 4.0 ppm for 500 ppm to 5000 ppm of microorganism is added to bind the microorganism pin flocks into large flocks.

A green algae from an outdoor open race way is harvested or separated from a waterbody, wherein coagulant dosage is reduced to about 150 ppm to 250 ppm upon combinatorial addition of coagulant and flocculant as described in the method of the instant disclosure.

To harvest or separate unialgal green algae from a waterbody, through combinatorial addition of coagulant and flocculant employed in the instant method, coagulant dosage is reduced to about 30 ppm to about 50 ppm, when compared to the dosages, which is as high as 10,000 ppm of coagulant in general harvesting or separating procedures.

Example 2: Demonstrates Reduction of Chemical Dosage During the Separation of Algae by Hybrid Electrocoagulation A waterbody comprising filamentous BGA (Particle type-III) is treated with the hybrid electro-coagulation, wherein the electrical conduction is passed and it is observed that the coagulant dosage is reduced to about 1 ppm. Similarly, when a waterbody comprising green algae (Particle type-I) is subjected to electrical conduction above the electrode potential of the metal electrode, wherein the coagulant dosage is reduced to about 0.6 ppm.

Further, a waterbody comprising non-filamentous BGA (Particle type-II) is subjected to electrical conduction above the electrode potential of the metal electrode, wherein the coagulant dosage is reduced to about 100 ppm. In the above described 3 independent experiments the flocculant concentration ranges from about 0.5 ppm to 4.0 ppm for a algal suspension of 500 ppm to 5000 ppm.

Example 3: Demonstrates the Reduction of Chemical Dosage During Separation of Algae by pH Modulated Coagulation-Flocculation A waterbody comprising solid particles such as microorganisms (e.g. an algal culture) is treated with pH modulated coagulation-flocculation approach of the present disclosure, it is observed that the coagulant dosage is reduced to about 2 to 3 times when compared to only chemical coagulation-flocculation approach. It is observed that modulating pH of the waterbody by addition of NaOH and maintaining the pH towards alkalinity reduces the consumption of coagulant during separation or harvesting of microorganism (e.g. algal culture). The alkaline pH observed to reduce the coagulant consumption is in the range of about 8.5 to about 11. The observed pattern of chemical consumption during pH modulated coagulation-flocculation and only coagulation-flocculation approach and pH induced flocculation is exemplified in FIG. 2.

Upon subjecting a waterbody comprising virgin culture to pH modulated coagulation-flocculation approach, it is observed that the coagulant dosage is reduced to about 50 ppm when compared to 150 ppm during only coagulation-flocculation approach without pH modulation.

Example 4: Demonstrates the Cost Effectiveness of pH Modulated Coagulation-Flocculation Approach The cost effectiveness of the pH modulated coagulation-flocculation based on example 3 is exemplified below in comparison to coagulation-flocculation approach and pH induced flocculation approach, respectively.

Below are the costs of chemicals based on quotes from different vendors:
Average cost for Coagulant=INR 60.0/Kg
Average cost for Flocculant=INR 120.0/Kg
Average cost of NaOH=INR 30.0/Kg.

- A waterbody comprising solid particles such as microorganism (e.g. a virgin algal cultural) is treated with only chemical coagulant-flocculant combination, wherein the pH of the culture is maintained similar to the original virgin algae culture pH i.e. 9.35, then the cost of harvesting is approximately about Rs. 91 of such waterbody with short sedimentation time of about greater than 30 seconds.
- If the pH modulation is employed exclusively without any other chemical addition and the pH of the waterbody comprising microorganism (eg virgin algal culture) is 10.1, the cost of harvesting is approximately about Rs.20/L of such waterbody, as it likely accompanied by long sedimentation time in the range of about 30 to 40 min. On the other hand, the cost of harvesting is approximately about Rs.65 Rs/L of such waterbody when the pH of the culture is adjusted to 10.5 without addition of coagulant and flocculant, wherein it is likely to be accompanied by short sedimentation time of about greater than 30 seconds.
- If the microorganisms (e.g. algal culture) is subjected to pH modulated coagulation-flocculation approach of the present disclosure, and wherein pH of the waterbody comprising an algal culture is initially adjusted to a pH of about 9.7 to about 10.0, followed by addition of coagulant(s) and flocculant(s) of the present disclosure, the cost of harvesting is approximately under Rs.5/L and the sedimentation time is about 30 seconds Thus, in conclusion from this example 4, it is inferred that pH modulated coagulation-flocculation approach results in cost savings of about 2 folds in comparison to chemical coagulation-flocculation approach, and about 4 to about 12 folds in comparison to only pH based flocculation. The cost effectiveness of pH modulated coagulation-flocculation approach is exemplified in FIG. 3.

Example 5: Illustrates Comparative Data of Method of the Present Disclosure Vis-à-Vis Techniques of the Prior Art The prior art techniques for separation or harvesting the cultures, preferably algae and/or bacteria from waterbody having cell densities not exceeding 0.5 g/L and salinity of the waterbody of about 4.0% which is an easier approach to harvest cultures from a waterbody.

On the other hand, the methods of the instant disclosure demonstrates separation or harvesting of cultures, preferably algae and/or bacteria from a waterbody having cell density of about 2.5 g/L and salinity of the waterbody of about 14%, which is considered to be extremely difficult condition to harvest or separate cultures. However, the methods of the instant disclosure has achieved separation or harvesting the cultures from such difficult condition cost effectively. Table-3 below illustrates the comparison of prior art techniques vis-à-vis method of the instant disclosure with regards to total OPEX (operating cost)

TABLE 3

Comparative data illustrating the Total OPEX of prior art techniques vis-à-vis methods of the present disclosure.

| Harvesting Technique | | Operating Cost [OPEX] | | |
|---|---|---|---|---|
| Primary | Secondary | OPEX Primary (USD/ Tonne of Biomass) | OPEX Secondary (USD/ Tonne of Biomass) | Total OPEX (USD/ Tonne of Biomass) |
| Centrifugation | Centrifugation | 1740 | | 1740 |
| Sedimentation | Filtration | 530-590.4 | 31.68-95.04 | 561.68-685.44 |
| Flotation (1) | Filtration | 267-299.5 | 31.68-95.05 | 298.68-394.55 |
| Flotation (2) | Filtration | 119.9 | 31.68-95.06 | 151.58-214.96 |
| Sedimentation | Centrifugation | 530-590.4 | 174.2 | 704.2-764.6 |
| Flotation (1) | Centrifugation | 267-299.5 | 174.2 | 441.2-473.7 |
| Flotation (2) | Centrifugation | 119.9 | 174.2 | 294.1 |
| pH Adjustment + Chemical-Coagulation + Electro-Coagulation + Chemical Flocculation (present disclosure) | | | | 176.51 |

The present disclosure in view of the above described illustrations and various embodiments, is thus able to successfully overcome the various deficiencies of prior art and provide for an improved method for separating solid particles, wherein suitable examples of the solid particles are living organisms, such as autotrophic organisms, preferably phototrophic organisms including but not limiting to algae from their environment, such as a waterbody including but not limiting to fresh water and marine water. Alternatively, the methods of present disclosure illustrates separation of solid particles including but not limiting to microorganism such as bacteria, organic matter or inorganic matter from a waterbody, including but not limiting to fresh water and marine water.

As used within the purview of the instant description, 'waterbody' means any surface comprising a liquid and is capable of supporting growth of any organic matter or living organism, preferably autotrophic, more preferably phototrophic organisms and dwelling non-living matter. The term waterbody preferably refers to marine water such as ocean water, sea water, and fresh water such as lake water, but it includes smaller pools of water such as pond, wetland, or more rarely, puddle.

As used within the purview of the instant description, 'solid particle' means any living or non-living matter capable of dwelling in a waterbody. The suitable examples of a solid particles is living organisms, preferably autotrophic, more preferably phototrophic organisms including but not limiting to algae, protists, phytoplankton, cyanobacteria and fungi.

Additional embodiments and features of the present disclosure will be apparent to one of ordinary skill in art based on the description provided herein. The embodiments herein provide various features and advantageous details thereof in the description. Descriptions of well-known/conventional methods and techniques are omitted so as to not unnecessarily obscure the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the word "comprise", or variations such as "comprises" or "comprising" wherever used, will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

We claim:

1. A method for separation of algae from a waterbody, said method comprising contacting the waterbody with an electric current to cause electrocoagulation, followed by contacting the waterbody with at least one coagulant and at least one flocculant to cause coagulation and flocculation, to separate the algae.

2. The method of claim 1, wherein the the algae is selected from the group consisting of *Scenedesmus* sp, *Cyanobacterium aponium, Nannochloropsis* sp, *Pseudooneochloris* sp, *Picochlorum* sp, *Nanochloropsis oceanica, Chlorella vulgaris, Chlorella sorokiniana*, and any combination of two or more thereof.

3. The method of claim 1, wherein the waterbody is selected from the group consisting of ocean water, sea water, lake water, pond water, wetland water, puddle water, and any combination thereof, and wherein the salinity of the waterbody is from about 0.1% to 14%.

4. The method of claim 1, wherein the at least one coagulant is at a concentration from about 5 ppm to 500 ppm for about 500 ppm to 5000 ppm of the algae in the waterbody; and the at least one flocculant is at a concentration from about 0.5 ppm to 4 ppm for about 500 ppm to 5000 ppm of the algae in the waterbody.

5. The method of claim 1, wherein a percentage separation or recovery of the algae from the waterbody is at least 95%.

6. The method of claim 1, wherein the combination of the at least one coagulant and the at least one flocculant causes coagulation and flocculation, respectively, of the algae in the waterbody.

7. The method of claim 1, wherein the electric current is contacted with the waterbody having the algae for a time duration of about 15 seconds to 720 seconds.

8. The method of claim 1, further comprising modulating the pH of the waterbody having the algae by adding a base selected from the group consisting of sodium hydroxide, potassium hydroxide, and a combination thereof, or by adding an acid selected from the group consisting of hydrochloric acid, nitric acid, sulphuric acid, and any combination thereof, prior to contacting the waterbody with the electric current.

9. The method of claim 8, wherein the pH of the waterbody upon addition of the base or the acid is from about 9.0 to 10.0.

10. The method of claim 1 further comprising a process selected from the group consisting of dissolved air flotation, froth flotation, and filtration for separation of the algae from the waterbody.

11. The method of claim 1, wherein the method is configured to reduce coagulant and flocculant dosage within the combination of the at least one coagulant and the at least one flocculant during the separation of the algae from the waterbody when compared to a method employing coagulant and flocculant, independently for separation of the algae.

12. The method of claim 1, wherein the at least one coagulant is selected from the group consisting of aluminum chlorohydrate polyamines, aluminum chlorohydrate-polyaluminum chloride-polyacrylamide-polyamines, ferric chloride, aluminum hydroxide chloride, a blend of cationic polymer with poly aluminum hydroxide, and any combination thereof, and the at least one flocculant is selected from the group consisting of copolymer of acrylamide and sodium acrylate, polyaluminum chloride, and any combination of two or more thereof.

* * * * *